(12) United States Patent
Zhao

(10) Patent No.: US 10,712,589 B2
(45) Date of Patent: *Jul. 14, 2020

(54) OPHTHALMIC APPARATUS WITH CORRECTIVE MERIDIANS HAVING EXTENDED TOLERANCE BAND BY MODIFYING REFRACTIVE POWERS IN UNIFORM MERIDIAN DISTRIBUTION

(71) Applicant: Johnson & Johnson Surgical Vision, Inc., Santa Ana, CA (US)

(72) Inventor: Huawei Zhao, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,885

(22) Filed: Mar. 23, 2017

(65) Prior Publication Data
US 2017/0273780 A1 Sep. 28, 2017

Related U.S. Application Data

(60) Provisional application No. 62/312,321, filed on Mar. 23, 2016, provisional application No. 62/312,338, filed on Mar. 23, 2016.

(51) Int. Cl.
*A61F 2/16* (2006.01)
*G02C 7/06* (2006.01)
(Continued)

(52) U.S. Cl.
CPC .............. *G02C 7/061* (2013.01); *A61F 2/164* (2015.04); *A61F 2/1613* (2013.01);
(Continued)

(58) Field of Classification Search
CPC .......................... A61F 2/1645; G02C 2202/02
See application file for complete search history.

(56) References Cited

U.S. PATENT DOCUMENTS 2,077,092 A    4/1937 Broder
3,305,294 A    2/1967 Alvarez
(Continued)

FOREIGN PATENT DOCUMENTS

CN    1035363 A    9/1989
CN    1039487 A    2/1990
(Continued)

OTHER PUBLICATIONS

International Search Report and Written Opinion for Application No. PCT/US2018/023946, dated Jun. 12, 2018, 16 pages.
(Continued)

*Primary Examiner* — David H Willse
*Assistant Examiner* — Javier G Blanco
(74) *Attorney, Agent, or Firm* — Johnson & Johnson Surgical Vision, Inc.

(57) ABSTRACT

The embodiments disclosed herein include improved toric lenses and other ophthalmic apparatuses (including, for example, contact lens, intraocular lenses (IOLs), and the like) and associated method for their design and use. The apparatus includes one or more optical zones, including an optical zone defined by a polynomial-based surface coincident at a plurality of meridians having distinct cylinder powers, wherein light incident to a given region of each of the plurality of meridians, and respective regions nearby, is directed to a given point of focus such that the regions nearby to the given region direct light to the given point of focus when the given meridian is rotationally offset from the given region, thereby establishing an extended band of operation, and wherein each of the plurality of meridians is uniformly arranged on the optical zone for a same given added power (in diopters) up to 1.0 D (diopters).

16 Claims, 12 Drawing Sheets

(51) Int. Cl.
*G02C 7/04* (2006.01)
*G02C 7/02* (2006.01)

(52) U.S. Cl.
CPC .......... *A61F 2/1618* (2013.01); *A61F 2/1645* (2015.04); *A61F 2/1654* (2013.01); *G02C 7/021* (2013.01); *G02C 7/028* (2013.01); *G02C 7/041* (2013.01); *G02C 7/042* (2013.01); *G02C 7/044* (2013.01); *G02C 7/06* (2013.01); *A61F 2/1643* (2015.04); *A61F 2240/002* (2013.01); *A61F 2250/0097* (2013.01); *G02C 2202/02* (2013.01); *G02C 2202/06* (2013.01); *G02C 2202/10* (2013.01); *G02C 2202/20* (2013.01); *G02C 2202/22* (2013.01)

(56) References Cited

U.S. PATENT DOCUMENTS

| | | |
|---|---|---|
| 3,367,734 A | 2/1968 | Karl et al. |
| 3,735,685 A | 5/1973 | Plummer |
| 4,010,496 A | 3/1977 | Neefe |
| 4,056,311 A * | 11/1977 | Winthrop ............... G02C 7/061 351/159.42 |
| 4,162,122 A | 7/1979 | Cohen |
| 4,210,391 A | 7/1980 | Cohen et al. |
| 4,319,564 A | 3/1982 | Karickhoff |
| 4,338,005 A | 7/1982 | Cohen |
| 4,340,283 A | 7/1982 | Cohen et al. |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,593,981 A | 6/1986 | Scilipoti |
| 4,605,409 A | 8/1986 | Kelman |
| 4,605,411 A | 8/1986 | Fedorov |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | Lemaster |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,114,220 A | 5/1992 | Baude |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,173,723 A | 12/1992 | Volk et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov |
| 5,278,592 A | 1/1994 | Marie et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,652,638 A | 7/1997 | Roffman et al. |
| 5,691,800 A | 11/1997 | Iki et al. |
| 5,699,142 A | 12/1997 | Lee et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 6,015,435 A | 1/2000 | Valunin et al. |
| 6,051,024 A | 4/2000 | Cumming |
| 6,055,111 A | 4/2000 | Nomura et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,261,321 B1 | 7/2001 | Kellan |
| 6,286,956 B1 | 9/2001 | Oyama et al. |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,598,606 B2 | 7/2003 | Terwee et al. |
| 6,609,793 B2 | 8/2003 | Norrby et al. |

(56) References Cited

U.S. PATENT DOCUMENTS

| | | |
|---|---|---|
| 6,705,729 B2 | 3/2004 | Piers et al. |
| 6,709,102 B2 | 3/2004 | Duppstadt |
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,425,068 B2 | 9/2008 | Koest |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,241,354 B2 | 8/2012 | Hong et al. |
| 8,740,382 B1 | 6/2014 | Liu et al. |
| 8,764,822 B2 | 7/2014 | Harris et al. |
| 8,862,447 B2 | 10/2014 | Weeber |
| 9,241,627 B2 | 1/2016 | Steinmueller |
| 9,393,108 B2 | 7/2016 | Canovas et al. |
| 9,491,431 B2 | 11/2016 | Zhou |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0021824 A1 | 2/2004 | Ye et al. |
| 2004/0021825 A1 | 2/2004 | Richardson |
| 2004/0054358 A1 | 3/2004 | Cox |
| 2004/0068317 A1 | 4/2004 | Knight |
| 2004/0080710 A1 | 4/2004 | Wooley et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2005/0096226 A1 | 5/2005 | Stock et al. |
| 2005/0122474 A1 | 6/2005 | Koretz |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0055877 A1 | 3/2006 | Yanari |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161914 A1 | 7/2008 | Brady et al. |
| 2008/0231809 A1 | 9/2008 | Haigis |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0234448 A1 | 9/2009 | Weeber et al. |
| 2009/0275929 A1 | 11/2009 | Zickler |
| 2009/0279048 A1 | 11/2009 | Hong et al. |
| 2009/0303465 A1 | 12/2009 | Clements et al. |
| 2009/0323020 A1 | 12/2009 | Zhao et al. |
| 2010/0016965 A1 | 1/2010 | Hong et al. |
| 2010/0082017 A1 | 4/2010 | Zickler et al. |
| 2010/0161048 A1 | 6/2010 | Schaper, Jr. |
| 2010/0220185 A1 | 9/2010 | Vertoprakhov et al. |
| 2010/0274234 A1 | 10/2010 | Liang |
| 2010/0315589 A1 | 12/2010 | Portney |
| 2011/0166652 A1 | 7/2011 | Bogaert et al. |
| 2011/0205486 A1 | 8/2011 | Zhao |
| 2012/0140166 A1 | 6/2012 | Zhao |
| 2012/0249955 A1 | 10/2012 | Sarver et al. |
| 2012/0310337 A1 | 12/2012 | Hacker et al. |
| 2012/0320334 A1 | 12/2012 | Ho et al. |
| 2013/0050637 A1 | 2/2013 | Roffman et al. |
| 2013/0307965 A1 | 11/2013 | Widman et al. |
| 2014/0016088 A1* | 1/2014 | De Rossi ............... G02C 7/061 351/159.42 |
| 2014/0135919 A1 | 5/2014 | Gontijo, IV et al. |
| 2014/0160436 A1 | 6/2014 | Kasthurirangan et al. |
| 2014/0268042 A1 | 9/2014 | Bor et al. |
| 2014/0293426 A1 | 10/2014 | Dobschal |
| 2015/0062529 A1 | 3/2015 | Kasthurirangan et al. |
| 2015/0138350 A1 | 5/2015 | Videcoq |
| 2015/0250583 A1 | 9/2015 | Rosen et al. |
| 2015/0320547 A1 | 11/2015 | Rosen et al. |
| 2015/0359625 A1 | 12/2015 | Argal et al. |
| 2015/0362746 A1 | 12/2015 | Skudder et al. |
| 2016/0157997 A1 | 6/2016 | Gerlach et al. |
| 2016/0299355 A1 | 10/2016 | Biemold et al. |

FOREIGN PATENT DOCUMENTS

| | | |
|---|---|---|
| CN | 1406120 A | 3/2003 |
| CN | 1833192 A | 9/2006 |
| CN | 102099729 A | 6/2011 |
| DE | 3107675 U1 | 7/1981 |
| DE | 3439551 A1 | 4/1986 |
| DE | 102005022683 A1 | 11/2006 |
| EP | 226400 A2 | 6/1987 |
| EP | 227357 A2 | 7/1987 |
| EP | 0343067 A1 | 11/1989 |
| EP | 0457553 A2 | 11/1991 |
| EP | 581198 A1 | 11/1995 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1310267 B1 | 1/2008 |
| EP | 1424049 B1 | 6/2009 |
| EP | 2182891 B1 | 4/2014 |
| FR | 2745711 A1 | 9/1997 |
| JP | H0255314 A | 2/1990 |

(56) References Cited

FOREIGN PATENT DOCUMENTS

| | | |
|---|---|---|
| WO | 3603961 A1 | 7/1986 |
| WO | 3109336 A1 | 6/1991 |
| WO | 3222264 A1 | 12/1992 |
| WO | 9303409 A1 | 2/1993 |
| WO | 9507487 A1 | 3/1995 |
| WO | 9856315 A1 | 12/1998 |
| WO | 9905499 A1 | 2/1999 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03009053 A1 | 1/2003 |
| WO | 2004034129 A1 | 4/2004 |
| WO | 2004090611 A2 | 10/2004 |
| WO | 2004096014 A2 | 11/2004 |
| WO | 05019906 A1 | 3/2005 |
| WO | 06025726 A1 | 3/2006 |
| WO | 2006032263 A2 | 3/2006 |
| WO | 2006047698 A1 | 5/2006 |
| WO | 06060477 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2008045847 A2 | 4/2008 |
| WO | 2008083283 A2 | 7/2008 |
| WO | 2009020963 A1 | 2/2009 |
| WO | 2009029515 A1 | 3/2009 |
| WO | 2009076670 A1 | 6/2009 |
| WO | 2009105567 A1 | 8/2009 |
| WO | 2009137491 A1 | 11/2009 |
| WO | 2010009254 A1 | 1/2010 |
| WO | 2010009257 A1 | 1/2010 |
| WO | 2012083143 A1 | 6/2012 |
| WO | 2012085917 A1 | 6/2012 |
| WO | 2012154597 A1 | 11/2012 |
| WO | WO 2015022215 A1 * | 2/2015 ........... A61F 2/1637 |
| WO | 2016123167 A1 | 8/2016 |

OTHER PUBLICATIONS

Abelman H., et al. "Tolerance and Nature of Residual Refraction in Symmetric Power Space as Principal Lens Powers and Meridians Change," Computational and Mathematical Methods in Medicine, 2014, vol. 2014, pp. 1-12.

Baumeister M., et al., "Tilt and Decentration of Spherical and Aspheric Intraocular Lenses: Effect on Higher-Order Aberrations," Journal of Cataract & Refractive Surgery, 2009, vol. 35 (6), pp. 1006-1012.

Brown W.L., "Revisions to Tolerances in Cylinder Axis and in Progressive Addition Lens Power in ANSI Z80.1-2005," Optometry, 2006, vol. 77 (7), pp. 343-349.

Canovas C., et al., "Customized Eye Models for Determining Optimized Intraocular Lenses Power," Biomedical Optics Express, Jun. 1, 2011, vol. 2 (6), pp. 1649-1662.

International Search Report and Written Opinion for Application No. PCT/US2017/023772, dated Jul. 21, 2017, 14 pages.

International Search Report and Written Opinion for Application No. PCT/US2017/023864, dated Jul. 6, 2017, 15 pages.

International Search Report and Written Opinion for Application No. PCT/US2017/023888, dated Jul. 24, 2017, 14 pages.

International Search Report and Written Opinion for Application No. PCT/US2017/023897, dated Jul. 11, 2017, 17 pages.

International Search Report and Written Opinion for Application No. PCT/US2017/023836, dated Jun. 19, 2017, 12 pages.

Olsen T., "Simple Method to Calculate the Surgically Induced Refractive Change," Journal of Cataract & Refractive Surgery, Mar. 1993, vol. 19 (2), pp. 319-320.

Hill W., et al., "Monte Carlo Simulation of Expected Outcomes with the Acrysof Toric Intraocular Lens," BMC Ophthalmology, Oct. 2008, vol. 8, pp. 22.

International Preliminary Report on Patentability for Application No. PCT/US2017/023772, dated Oct. 4, 2018, 7 pages.

Mencucci R., et al., "Clinical outcomes and rotational stability of a 4-haptic toric intraocular lens in myopic eyes," Journal of Cataract & Refractive Surgery, Sep. 2014, vol. 40 (9), pp. 1479-1487.

Einighammer J., et al., "The Individual Virtual Eye: a Computer Model for Advanced Intraocular Lens Calculation, " Journal of optometry, Apr.-Jun. 2009, vol. 2 (2), pp. 70-82.

Gobin L., et al., "Spherotoric Bag-In-The-Lens Intraocular Lens: Power Calculation and Predictive Misalignment Nomogram, " Journal of Cataract & Refractive Surgery, Jun. 2011, vol. 37 (6), pp. 1020-1030.

Naeser K., "Assessment and Statistics of Surgically Induced Astigmatism, " Acta Ophthalmologica, May 2008, vol. 36 Suppl 1, pp. 5-28.

Narvaez J., et al., "Accuracy of Intraocular Lens Power Prediction Using the Hoffer Q, Holladay 1, Holladay 2, and SRK/T formulas, " Journal of Cataract & Refractive Surgery, Dec. 2006, vol. 32 (12), pp. 2050-2053.

Patel S., et al., "An Evaluation of Unexpected Refractive Outcomes Following Toric IoL Implantation for Astigmatism: A Sector Subtraction Graphical Method for Calculating the Effective Astigmatic Correction, " Research Sate, Jan. 2016, 90 Reads.

Alfonso J.F., et al., "Prospective Study of the Acri.LISA Bifocal Intraocular Lens," Journal of Cataract Refractive Surgery, Nov. 2007, vol. 33 (11), pp. 1930-1935.

Alio J.L., et al., "Phakic Anterior Chamber Lenses for the Correction of Myopia: A 7-Year Cumulative Analysis of complications in 263 Cases," Ophthalmology, Mar. 1999, vol. 106 (3), pp. 458-466.

Apple D.J., et al., "Anterior Chamber Lenses Part 1: Complications and Pathology and a Review of Designs," Journal of Cataract Refractive Surgery, Mar. 1987, vol. 13 (2), pp. 157-174.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.

Baikoff G., et al., "Angle-fixated Anterior Chamber Phakic Intraocular Lens for Myopia 7 to -19 Diopters," Journal of Refractive Surgery, May-Jun. 1998, vol. 14 (3), pp. 282-292.

Canovas C., et al., "Hybrid Adaptive-Optics Visual Simulator," Optical Letters, Jan. 15, 2010, vol. 35 (2), pp. 196-198.

Cheng X., et al., "Predicting Subjective Judgment of Best Focus with Objective Image Quality Metrics," Journal of Vision, Apr. 2004, vol. 4 (4), pp. 310-321.

CILCO Advertisement Brochure, Oct. 1982, 3 pages.

Cohen A.L., "Practical Design of a Bifocal Hologram Contact Lens or Intraocular Lens," Applied Optics, Jul. 1, 1992, vol. 31 (19), pp. 3750-3754.

De Almeida M.S., et al., "Different Schematic Eyes and their Accuracy to the in Vivo Eye: A Quantitative Comparison Study," Brazilian Journal of Physics, Jun. 2007, Vol. 37 (2A), 10 pages.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, Apr. 1992, vol. 1780, pp. 393-402.

Egger J.R., "Use of Fresnel Lenses in Optical Systems: Some Advantages and Limitations," in: Atomic and Molecular Spectroscopy, vol. 193, Paul R. Yoder, Jr., ed., SPIE Proceedings, the International Society for Optical Engineering, 1979, pp. 63-69.

Farberov, "Manufacturing Fresnel Lenses for Cameras," Soviet Journal of Optical Technology, 1983, vol. 50 (3), pp. 186-188.

Gupta P.A., "Theoretical Analysis of the Fresnel lens As a Function of Design Parameters," Applied Energy, 1981, vol. 9 (4), pp 301-310.

(56) References Cited

OTHER PUBLICATIONS

Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.

Liou H.L. et al. "Anatomically Accurate, Finite Model Eye for Optical Modeling," Journal of Optical Society of America, Aug. 1997, vol. 14 (8), pp. 1684-1695.

Liou H.L., et al., "The Prediction of Spherical Aberration with Schematic Eyes," Ophthalmic and Physiological Optics, Jan. 1996, vol. 16 (4), pp. 348-354.

Marinho A., "Results are Encouraging for Phakic IOLs, but More Work is needed," Refractive Surgery, Feb. 2000, p. 12, 15.

Marsack J.D., et al., "Metrics of Optical Quality Derived from Wave Aberrations Predict Visual Performance," Journal of Vision, Apr. 2004, vol. 4 (4), pp. 322-328.

Menapace R., "The Capsular Tension Rings," Journal of Cataract & Refractive Surgery, Dec. 10, 2008, Chap. 3, pp. 27-44.

Monsoriu J.A., et al., "Devil's Lenses," Optics Express, Oct. 17, 2007, vol. 15 (21), pp. 13858-13864.

Navarro R., et al., "Accommodation-Dependent Model of the Human Eye with Asperics," Journal of the Optical Society of America, Aug. 1985, vol. 2 (8), pp. 1273-1281.

Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.

Norrby S., et al., "Model Eyes for Evaluation of Intraocular Lenses," Applied Optics, Sep. 7, 2007, vol. 46 (26), pp. 6595-6605.

Piers P.A., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Praeger D.L, "Praeger Technique for the Insertion of the Copeland Radial Iol Posterior Chamber Placement," aopeland Lens, 1982, 7 pages.

Siedlecki D., et al., "Radial Gradient index Intraocular Lens: A Theoretical Model," Journal of Modern Optics, Feb. 20-Mar. 10, 2008, vol. 55 (4-5), pp. 639-647.

Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.

Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Vanderwerf D., et al., "Approximating the Fresnel Lens," Electro Optical Systems Design, 1982, pp. 47-52.

Vass C., et al., "Prediction of Pseudophakic Capsular bag Diameter based on Biometric Variables," Journal of Cataract and Refractive Surgery, Oct. 1999, vol. 25 (10), pp. 1376-1381.

Villegas E.A., et al., "Correlation between Optical and Psychophy, Sical Parameters as a Function of Defocus," Optometry and Vision Science, Jan. 1, 2002, vol. 79 (1), pp. 60-67.

\* cited by examiner

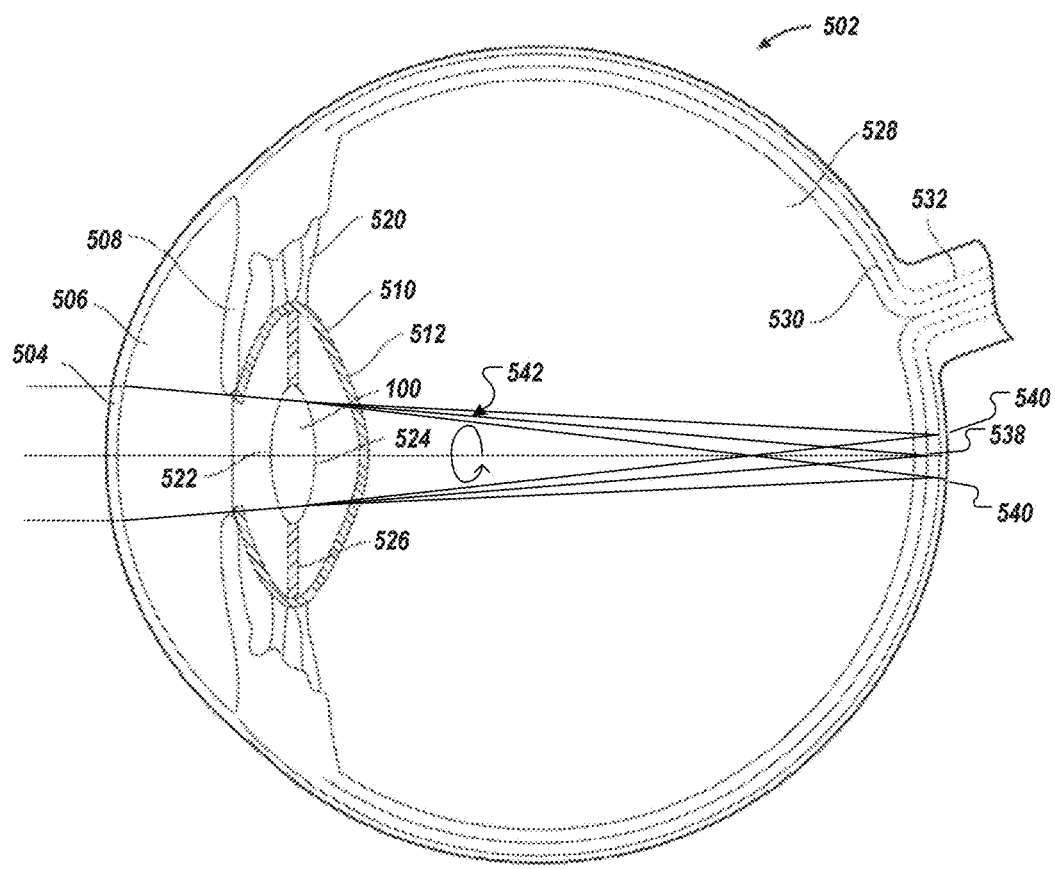
FIG. 5
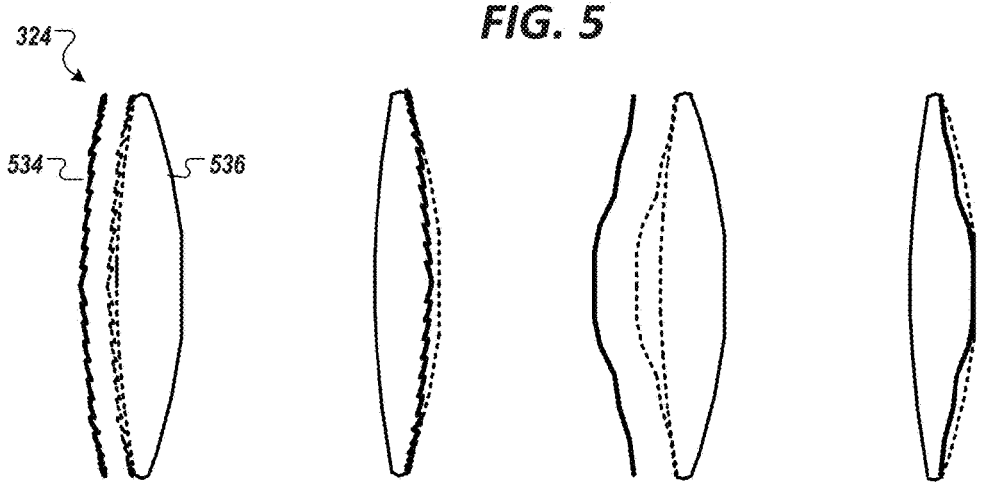
FIG. 6A  FIG. 6B  FIG. 6C  FIG. 6D

OPHTHALMIC APPARATUS WITH CORRECTIVE MERIDIANS HAVING EXTENDED TOLERANCE BAND BY MODIFYING REFRACTIVE POWERS IN UNIFORM MERIDIAN DISTRIBUTION

RELATED APPLICATIONS

This application claims priority to, and the benefit of, U.S. Provisional Appl. No. 62/312,321, filed Mar. 23, 2016 and U.S. Provisional Appl. No. 62/312,338, filed Mar. 23, 2016, each of which is incorporated by reference herein in its entirety.

TECHNICAL FIELD

This application is directed to lenses for correcting astigmatism, including providing increased tolerance for lens placement during implantation.

BACKGROUND

Ophthalmic lenses, such as spectacles, contact lenses and intraocular lenses, may be configured to provide both spherical and cylinder power. The cylinder power of a lens is used to correct the rotational asymmetric aberration of astigmatism of the cornea or eye, since astigmatism cannot be corrected by adjusting the spherical power of the lens alone. Lenses that are configured to correct astigmatism are commonly referred to as toric lenses. As used herein, a toric lens is characterized by a base spherical power (which may be positive, negative, or zero) and a cylinder power that is added to the base spherical power of the lens for correcting astigmatism of the eye.

Toric lenses typically have at least one surface that can be described by an asymmetric toric shape having two different curvature values in two orthogonal axes, wherein the toric lens is characterized by a "low power meridian" with a constant power equal to the base spherical power and an orthogonal "high power meridian" with a constant power equal to the base spherical power plus the cylinder power of the lens. Intraocular lenses, which are used to replace or supplement the natural lens of an eye, may also be configured to have a cylinder power for reducing or correcting astigmatism of the cornea or eye.

Existing toric lenses are designed to correct astigmatic effects by providing maximum cylindrical power that precisely matches the cylinder axis. Haptics are used to anchor an intraocular lens to maintain the lenses at a desired orientation once implanted in the eye. However, existing toric lenses themselves are not designed to account for misalignment of the lens that may occur during surgical implantation of the lens in the eye or to account for unintended post-surgical movement of the lens in the eye.

One type of toric lens design includes angularly-varying phase members that extend depth of focus features to extend the tolerance band of an intended correction meridian. However, lens design that extends the astigmatism tolerance of a toric IOL are not commonplace.

Accordingly, it would be desirable to have more intraocular lens designs that are tolerant to misalignments.

SUMMARY

The embodiments disclosed herein include improved toric lenses and other ophthalmic apparatuses (including, for example, contact lens, intraocular lenses (IOLs), and the like) and associated method for their design and use. In an aspect, an ophthalmic apparatus is disclosed having regions of one or more base spherical powers and one or more cylinder powers that are added to the one or more base spherical power for correcting an astigmatism (e.g., an intended astigmatism). The apparatus includes one or more optical zones, including an optical zone defined by a polynomial-based surface coincident at a plurality of meridians having distinct cylinder powers, wherein light incident to a given region of a given meridian of each of the plurality of meridians, and respective regions nearby, is directed to a given point of focus such that the regions nearby to the given region direct light to the given point of focus when the given meridian is rotationally offset from the given region, thereby establishing an extended band of operation, and wherein each of the plurality of meridians is uniformly arranged on the optical zone for a same given added power (in diopters) up to 1.0 D (diopters), here preferably each 0.5 D (diopters).

In some embodiments, the meridians are uniformly arranged on the optical zones at about 0.01 D (diopters). In some embodiments, the meridians are uniformly arranged on the optical zones at about 0.05 D (diopters). In some embodiments, the meridians are uniformly arranged on the optical zones at about 0.1 D (diopters). In some embodiments, the meridians are uniformly arranged on the optical zones at about 0.15 D (diopters). In some embodiments, the meridians are uniformly arranged on the optical zones at about 0.2 D (diopters). In some embodiments, the meridians are uniformly arranged on the optical zones at about 0.25 D (diopters). In some embodiments, the meridians are uniformly arranged on the optical zones at about 0.3 D (diopters). In some embodiments, the meridians are uniformly arranged on the optical zones at about 0.35 D (diopters). In some embodiments, the meridians are uniformly arranged on the optical zones at about 0.4 D (diopters). In some embodiments, the meridians are uniformly arranged on the optical zones at about 0.45 D (diopters). In some embodiments, the meridians are uniformly arranged on the optical zones at about 0.5 D (diopters). In some embodiments, the meridians are uniformly arranged on the optical zones at about 0.55 D (diopters). In some embodiments, the meridians are uniformly arranged on the optical zones at about 0.6 D (diopters). In some embodiments, the meridians are uniformly arranged on the optical zones at about 0.65 D (diopters). In some embodiments, the meridians are uniformly arranged on the optical zones at about 0.7 D (diopters). In some embodiments, the meridians are uniformly arranged on the optical zones at about 0.75 D (diopters). In some embodiments, the meridians are uniformly arranged on the optical zones at about 0.8 D (diopters). In some embodiments, the meridians are uniformly arranged on the optical zones at about 0.85 D (diopters). In some embodiments, the meridians are uniformly arranged on the optical zones at about 0.95 D (diopters). In some embodiments, the meridians are uniformly arranged on the optical zones at about 1.0 D (diopters).

In some embodiments, differences among each continuously uniformly distributed contour line, at a given IOL plane, associated with a given meridian of the plurality of meridians is less than about 0.6 D (diopters).

In some embodiments, the polynomial-based surface establishes the extended band of operation across a range selected from the group consisting of about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the polynomial-based surface is characterized by a series of weighted cosine-based function.

In some embodiments, the plurality of meridians include a first meridian, a second meridian, and a third meridian, each having the extended band of operation of at least 10 degrees.

In some embodiments, a first center of the first meridian is angularly spaced about 90 degrees to a second center of the second meridian.

In some embodiments, the optical zone comprises a fourth meridian having an accumulated high surface amplitude such that the first meridian, the second meridian, and the third meridian have the established extended band of operation.

In some embodiments, the fourth meridian is purposely positioned at an angular position that coincides with a diagnosed limited retinal functional area of a patient.

In some embodiments, the polynomial-based surface comprises a refractive surface.

In some embodiments, the polynomial-based surface comprises a diffractive surface.

In some embodiments, an offset of each meridian of the plurality of meridians of about 10 degrees causes a MTF (modulation transfer function) measure change of less than 10% at 30 cycles per degree (cpd).

In some embodiments, the polynomial-bases surface at a first meridian and at a second meridian comprises a bifocal monofocal lens.

In some embodiments, the polynomial-bases surface at a first meridian comprises a monofocal lens.

In some embodiments, the polynomial-bases surface at a first meridian comprises an extended range lens.

In another aspect, a rotationally-tolerant ophthalmic apparatus is disclosed that is configured to correct astigmatism. The ophthalmic apparatus includes a multi-zonal lens body having a plurality of optical zones configured to apply cylinder power at an astigmatism meridian of an eye. The multi-zonal lens body forming a angularly-varying phase member having a peak cylinder power centered at an astigmatism correcting meridian, the angularly-varying phase member at the peak cylinder power being configured to direct light to a first point of focus on the retina, and the angularly-varying phase member varies, at each optical zone, along meridians nearby to the astigmatism correcting meridian to direct light to points of focus nearby to the first point of focus such the multi-zonal lens body, when rotational offset from the peak cylinder power, directs light from the nearby points of focus to the first point of focus, thereby establishing a band of operational meridians over the astigmatism meridian. The angularly-varying phase member has a profile that is uniformly spaced for every 0.5 D (diopters).

In some embodiments, the band of operation is established across a range selected from the group consisting of about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the polynomial-based surface is characterized by a series of weighted cosine-based function.

In some embodiments, the angularly-varying phase member has a band of operation of at least 10 degrees.

In some embodiments, the multi-zonal lens body forms a second angularly-varying phase member having a second peak cylinder power centered at a second correcting meridian, the second angularly-varying phase member at the second peak cylinder power being configured to direct light to a second point of focus on the retina. The second angularly-varying phase member varies, at each optical zone, along meridians nearby to the second correcting meridian to direct light to points of focus nearby to the second point of focus such the multi-zonal lens body, when rotational offset from the second peak cylinder power, directs light from the nearby points of focus to the second point of focus, and the second angularly-varying phase member has the profile that is uniformly spaced for every 0.5 D (diopters).

In some embodiments, the multi-zonal lens body forms a second angularly-varying phase member having a second peak cylinder power centered at a second correcting meridian, the second angularly-varying phase member at the second peak cylinder power being configured to direct light to a second point of focus on the retina. The second angularly-varying phase member varies, at each optical zone, along meridians nearby to the second correcting meridian to direct light to points of focus nearby to the second point of focus such the multi-zonal lens body, when rotational offset from the second peak cylinder power, directs light from the nearby points of focus to the second point of focus. The second angularly-varying phase member has a second profile that is uniformly spaced for every about 0.5 D (diopters).

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 5 is a schematic drawing of a top view of a human eye, in which the natural lens of the eye has been removed and replaced with an ophthalmic apparatus that includes an exemplified freeform-polynomial surface area, in accordance with an illustrative embodiment.

FIGS. 6A, 6B, 6C, and 6D are schematic diagrams of exemplary ophthalmic apparatuses that include either refractive or diffractive freeform-polynomial surfaces, in accordance with an illustrative embodiment.

DETAILED DESCRIPTION OF THE PREFERRED EMBODIMENT

Each and every feature described herein, and each and every combination of two or more of such features, is included within the scope of the present invention provided that the features included in such a combination are not mutually inconsistent.

Embodiments of the present invention are generally directed to toric lenses or surface shapes, and/or related methods and systems for fabrication and use thereof. Toric lenses according to embodiments of the present disclosure find particular use in or on the eyes of human or animal subjects. Embodiments of the present disclosure are illustrated below with particular reference to intraocular lenses; however, other types of lenses fall within the scope of the present disclosure. Embodiments of the present disclosure provide improved ophthalmic lens (including, for example, contact lenses, and intraocular lenses, corneal lenses and the like) and include monofocal refractive lenses, monofocal diffractive lenses, bifocal refractive lenses, bifocal diffractive lenses, and multifocal refractive lenses, multifocal diffractive lenses.

As used herein, the term "refractive optical power" or "refractive power" means optical power produced by the refraction of light as it interacts with a surface, lens, or optic. As used herein, the term "diffractive optical power" or "diffractive power" means optical power resulting from the diffraction of light as it interacts with a surface, lens, or optic.

As used herein, the term "optical power" means the ability of a lens or optics, or portion thereof, to converge or diverge light to provide a focus (real or virtual), and is commonly specified in units of reciprocal meters (m−1) or Diopters (D). When used in reference to an intraocular lens, the term "optical power" means the optical power of the intraocular lens when disposed within a media having a refractive index of 1.336 (generally considered to be the refractive index of the aqueous and vitreous humors of the human eye), unless otherwise specified. Except where noted otherwise, the optical power of a lens or optic is from a reference plane associated with the lens or optic (e.g., a principal plane of an optic). As used herein, a cylinder power refers to the power required to correct for astigmatism resulting from imperfections of the cornea and/or surgically induced astigmatism.

As used herein, the terms "about" or "approximately", when used in reference to a Diopter value of an optical power, mean within plus or minus 0.25 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

Figure 1:
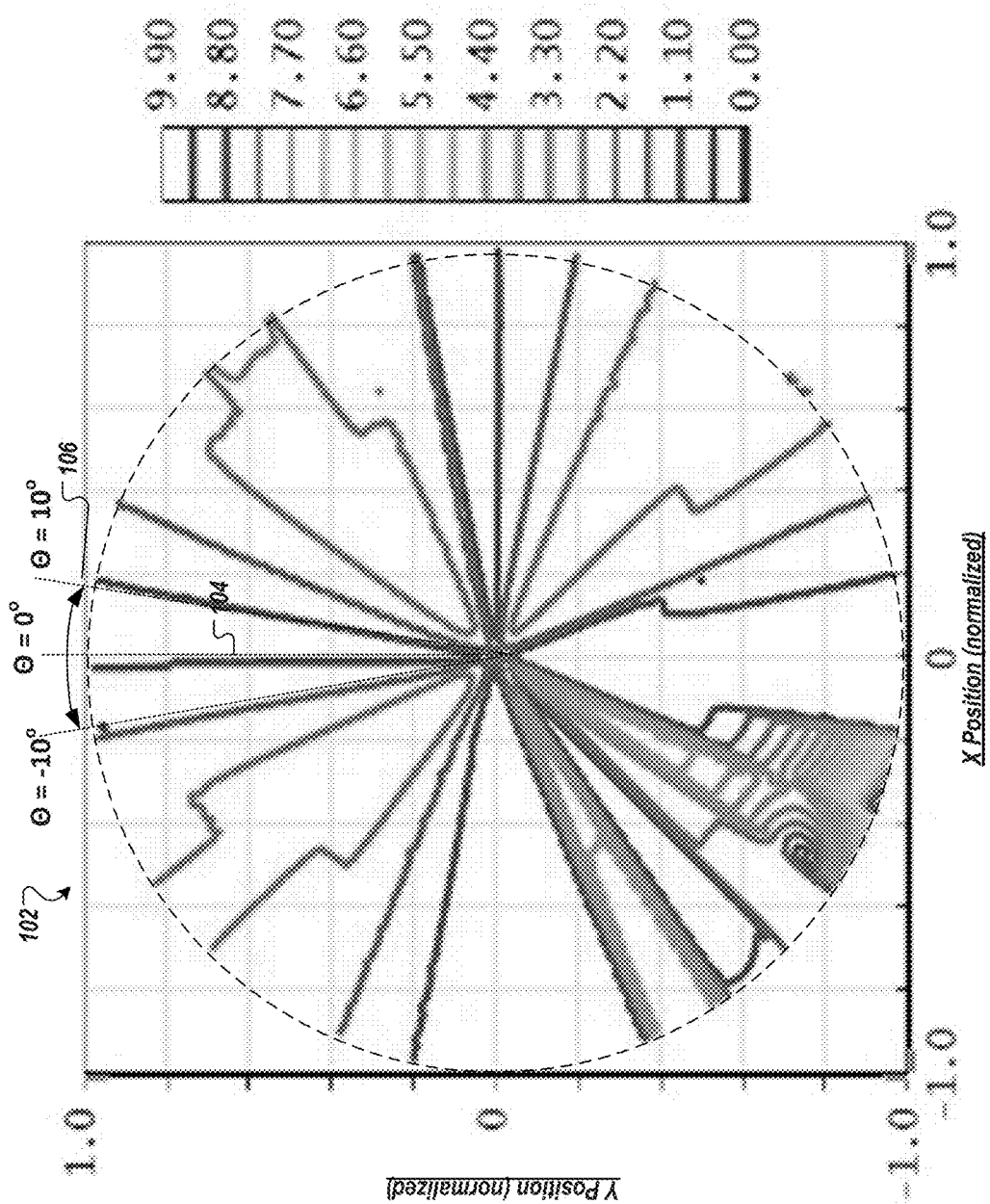
FIG. 1 is a diagram of a polynomial surface that is uniformly arranged over a plurality of meridians that provides extended rotational tolerance, in accordance with an illustrative embodiment.

FIG. 1 is a diagram of cylindrical map of a polynomial surface 102 (also referred to as an ETA polynomial surface 102) that is uniformly arranged over a plurality of meridians that provides extended rotational tolerance, in accordance with an illustrative embodiment. The polynomial surface 102 is mapped to a surface of an ophthalmic apparatus 100 (not shown—see FIG. 6) to provide cylinder power to the ophthalmic apparatus, e.g., for the correction an astigmatism, or the like, such that the ophthalmic apparatus can be subjected to a cylindrical axis misalignment (CAM) (shown via arrow 104) of the meridian 106a of up to 10 degrees without degradation of the corrective performance (e.g., with regard to visual acuity (VA) or modular transfer function (MTF)), as compared to when there no misalignment.

Notably, the polynomial surface 102 is uniformly arranged, in this embodiment, over a plurality of meridians 106 for every 0.5 D (diopters). It should be appreciated that other values can be used. In some embodiments, the polynomial surface 102 is uniformly arranged over a plurality of meridians 106 for every 0.41 D (diopters). In some embodiments, the polynomial surface 102 is uniformly arranged over a plurality of meridians 106 for every 0.42 D (diopters). In some embodiments, the polynomial surface 102 is uniformly arranged over a plurality of meridians 106 for every 0.44 D (diopters). In some embodiments, the polynomial surface 102 is uniformly arranged over a plurality of meridians 106 for every 0.46 D (diopters). In some embodiments, the polynomial surface 102 is uniformly arranged over a plurality of meridians 106 for every 0.45 D (diopters). In some embodiments, the polynomial surface 102 is uniformly arranged over a plurality of meridians 106 for every 0.48 D (diopters). In some embodiments, the polynomial surface 102 is uniformly arranged over a plurality of meridians 106 for every 0.52 D (diopters). In some embodiments, the polynomial surface 102 is uniformly arranged over a plurality of meridians 106 for every 0.54 D (diopters). In some embodiments, the polynomial surface 102 is uniformly arranged over a plurality of meridians 106 for every 0.56 D (diopters). In some embodiments, the polynomial surface 102 is uniformly arranged over a plurality of meridians 106 for every 0.58 D (diopters). In some embodiments, the polynomial surface 102 is uniformly arranged over a plurality of meridians 106 for every 0.60 D (diopters). The number of the added power at which the meridian are uniformly distributed is set at an individual eye's tolerance of meridian power change such as the astigmatic or cylinder power. This value changes individually, up to 1.0 D (diopters), but on average a comfortable tolerance is about 0.5 D at the IOL plane.

The angularly-varying phase members, in some embodiments, include an optimized combination of angularly and zonally diffractive (or refractive) phase structure located at each meridian to vary the extended depth of focus to a plurality of nearby focus points. Light directed to such nearby focus points are thus directed to the desired focus point when the ophthalmic apparatus is subjected to a rotational offset from a primary intended axis of alignment, thereby extending the rotational tolerance of the apparatus to an extended tolerance band. This may also be referred to as "extended tolerance astigmatism band" or "extended misalignment band." Remarkably, this extended tolerance astigmatism band delivers cylinder power to correct for the astigmatism for a range of meridians (e.g., up to ±10° or more as shown in FIG.1), thereby eliminating any need for additional corrective measures (e.g., supplemental corrective devices or another surgical intervention) when the implanted ophthalmic apparatus is not perfectly aligned to the desired astigmatism meridian in the eye.

Put another way, the angularly-varying phase members facilitate an extended band of the corrective meridian that has minimal, and/or clinically acceptable, degradation of the visual acuity and modulation transfer function when the ophthalmic apparatus is subjected to rotational misalignment between the astigmatic axis and a center axis of the corrective meridian.

Figure 2:
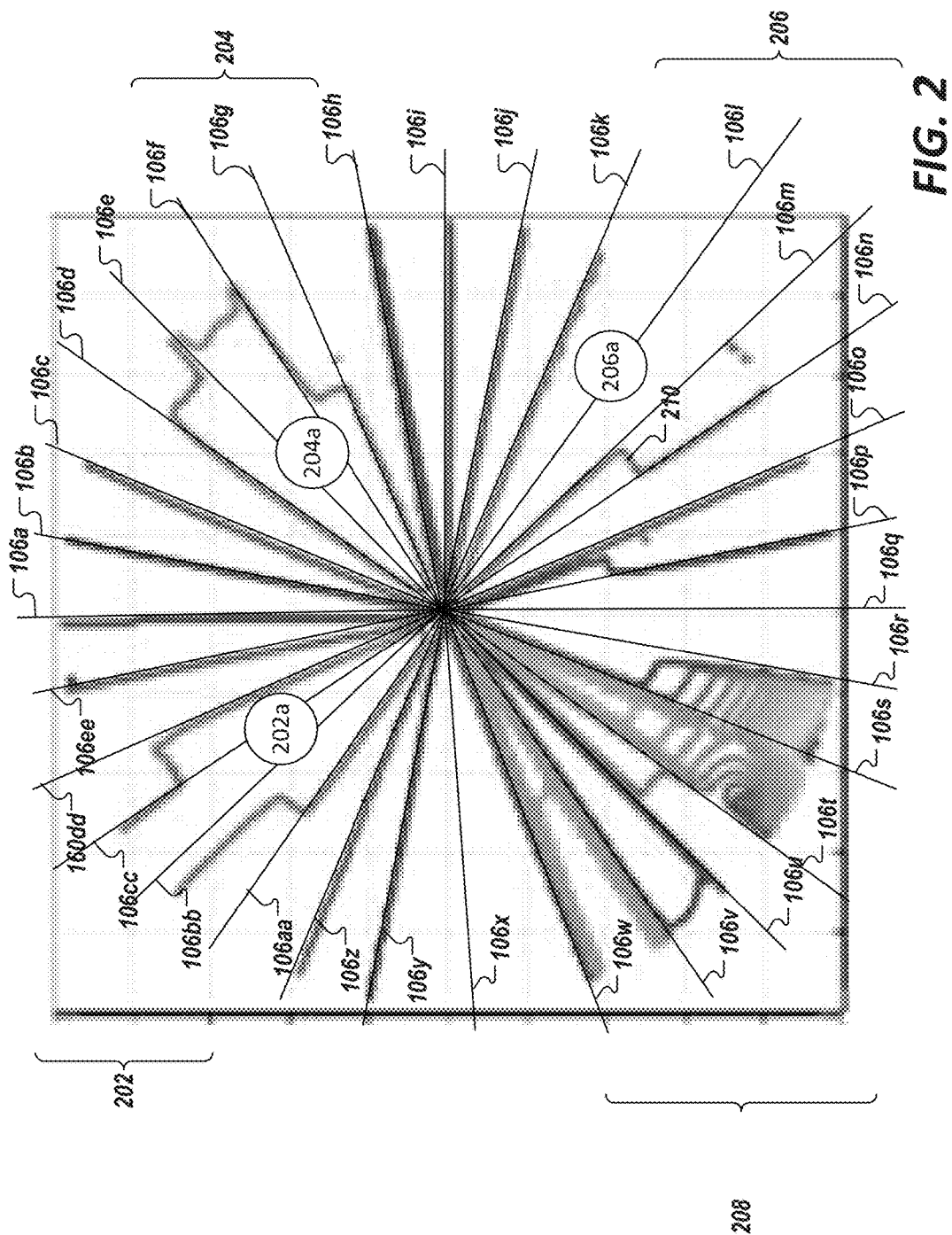
FIG. 2 is a diagram of the polynomial surface of FIG. 1 shown with the plurality of uniformly arranged meridians, in accordance with an illustrative embodiment.

FIG. 2 is a diagram of the ETA polynomial surface 102 of FIG. 1 shown with the plurality of uniformly arranged meridians 106 (shown as 106a-106ee), in accordance with an illustrative embodiment. As shown in FIG. 2 (and in FIG. 1), the ETA polynomial surface 102, in this example, includes three regions 202, 204, 206 (the center shown as 202a, 204a, and 206a) of corrective cylindrical power—the first region 202 spanning between meridians 106aa and 106dd; the second region 204 spanning between meridians 106d and 106g; and the third region 206 spanning between meridians 106k and 106n. As shown, each of the meridians (106a-106q and 106x-106a) are uniformly arranged (i.e., uniformly spaced at various angular positions—here about 11 degrees apart) for every 0.5 D (diopters).

As shown in FIG. 2, meridian 106a is located at about 90 degrees; meridian 106b is located at about 79 degree; meridian 106c is located at about 67 degree; meridian 106d is located at about 55 degree; meridian 106e is located at about 44 degree; meridian 106f is located at about 33 degree; meridian 106g is located at about 24 degree; meridian 106h is located at about 11 degree; meridian 106i is located at about 0 degree; meridian 106j is located at about −12 degree; meridian 106k is located at about −24 degree; meridian 106l is located at about −36 degree; meridian 106m is located at about −47 degree; meridian 106n is located at about −56 degree; meridian 106o is located at about −67 degree; meridian 106p is located at about −79 degree; and meridian 106q is located at about −90 degree; meridian 106r is located at about −100 degree; meridian 106s is located at about −112 degree; meridian 106t is located at about −125 degree; meridian 106u is located at about −135 degree; meridian 106v is located at about −145 degree; meridian 106w is located at about −158 degree; meridian 106x is located at about −176 degree; meridian 106y is located at about 168 degree; meridian 106z is located at about 157 degree; meridian 106aa is located at about 145 degree; meridian 106bb is located at about 133 degree; meridian 106cc is located at about 123 degree; meridian 106dd is located at about 113 degree; and meridian 106ee is located at about 101 degree.

It is contemplated that the ETA polynomial surface 102 may include more than three regions of corrective cylindrical power, e.g., a fourth region, a fifth region, and etc. In such embodiments, the regions between the corrective meridians may be uniformly reduced, e.g., to about 10 degrees apart, about 9 apart, about 8 degrees apart, about 7 degrees apart, and etc.

Table 1 illustrates examples of toric IOL designs with meridians uniformly distributed for a same added power, for a 0.25 D same added power, for a 0.5 D same added power, for a same 0.75 D same added power, and for a same 1.0 D same added power.

TABLE 1

| Added Power (in diopters) between each meridian | Max Added Power (diopters) | Number of meridians (from low to low power over ¼ of the lens) | Max number of corrective regions |
|---|---|---|---|
| 0.25 D | 4 D | 16 (4/0.25) | 6 |
| 0.5 D | 4 D | 8 (4/0.5) | 3 |
| 0.75 D | 4 D | 5.3 (4/0.75) | 3 |
| 1.0 D | 4 D | 4 (4/1) | 3 |

As shown in Table 1, when the meridians are uniformly arranged for a same added power of 0.5 D, for a 4 D base, there are 8 meridians between the high power meridian and the low power meridian in a quadrant of the polynomial surface between meridian 106a and 106i. This allows for up to 3 corrective regions on the polynomial surface, as shown in FIG. 2. In another embodiment, when the meridians are uniformly arranged for a same added power of 0.75 D, for a 4 D base, there are 5.4 meridians between the high power meridian and the lower power. This allows up to 3 corrective regions of the polynomial surface. In another embodiment, when the meridians are uniformly arranged for a same added power of 0.25 D, for a 4 D base, there are 16 meridians between the high power meridian and the lower power. This allows up to 6 corrective regions of the polynomial surface. In another embodiment, when the meridians are uniformly arranged for a same added power of 1.0, for a 4 D base, there are 2 meridians between the high power meridian and the lower power. This allows up to 3 corrective regions of the polynomial surface, which has the high power meridian center located at meridians 106e, 106s, and 106cc.

Figure 3:
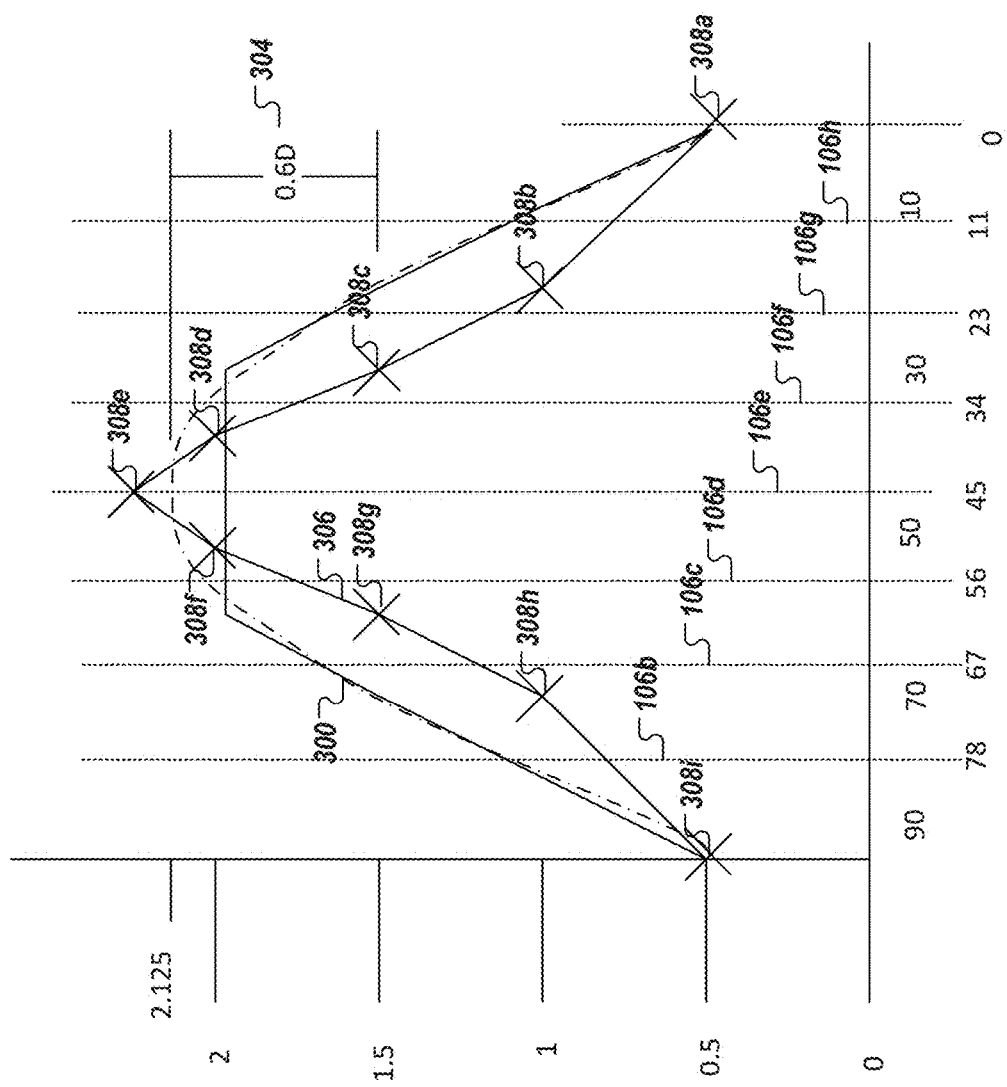
FIG. 3 is a profile of the polynomial surface of FIG. 1 with the plurality of uniformly arranged meridians, in accordance with an illustrative embodiment.

FIG. 3 is a profile 300 of the polynomial surface of FIG. 1 with the plurality of uniformly arranged meridians, in accordance with an illustrative embodiment. As shown in FIG. 3, each meridian (e.g., 106b, 106c, 106d, 106e, 1060 is defined by an angular position that is uniformly arranged, about 11 degrees apart, for every 0.5 D (diopters). In addition, the majority of meridian power change, from one meridian to the next, generates a change of more than 0.6 D power difference (shown as 304). The result is a profile 300 that is more uniformly sloped that provided extended range of operation beyond about 5 degrees of misalignment (e.g., up to 10 degrees misalignment), as compared to a conventional or macro regular cylindrical surface with power changes according to COS(2*theta) trend, for a given difference between two meridians, shown as profile 306. As shown in profile 306, the meridian distribution is not uniform. Specifically, the meridian (in degrees) from the minimum power meridian—namely 0 degrees (308a)—is located at a 20.7-degree position (308b), a 30-degree position (308c), a 37.8-degree position (308d), a 45.0-degree position (308e), a 52.2-degree position (308f), a 60-degree position (308g), a 69.3-degree position (308h), a 90.0-degree position (308i), and etc., in a periodic trend, which provides a non-uniform meridian difference of about 20.7 degrees (between 308a and 308b), about 9.3 degrees (between 308b and 308c), about 7.8 degrees (between 308c and 308d), about 7.2 degrees (between 308d and 308e), about 7.2 degrees (between 308e and 308f), about 7.8 degree (between 308f and 308g), about 9.3 (between 308g and 308h), and about 20.7 degree (between 308h and 308i).

Referring still to FIG. 3, off-center structures of the polynomial surface 102 extend from the center structure in a gradually varying manner to apply cylinder power to a band of meridians surrounding the corrective meridian enabling the ophthalmic apparatus to operate off-axis (or off-meridian) to the corrective meridian (e.g., the astigmatism meridian). Notably, there are no more than 0.6-Diopter difference between any neighboring uniformly distributed contour lines.

In some embodiments, the polynomial surface 102 is defined by a combination of spline or polynomial (e.g., a Zernike polynomial, a Chebyshev polynomial, or a combination of both) that is constrained by the condition of the meridians being uniformly arranged apart for every 0.5 D (diopters).

Figure 4:
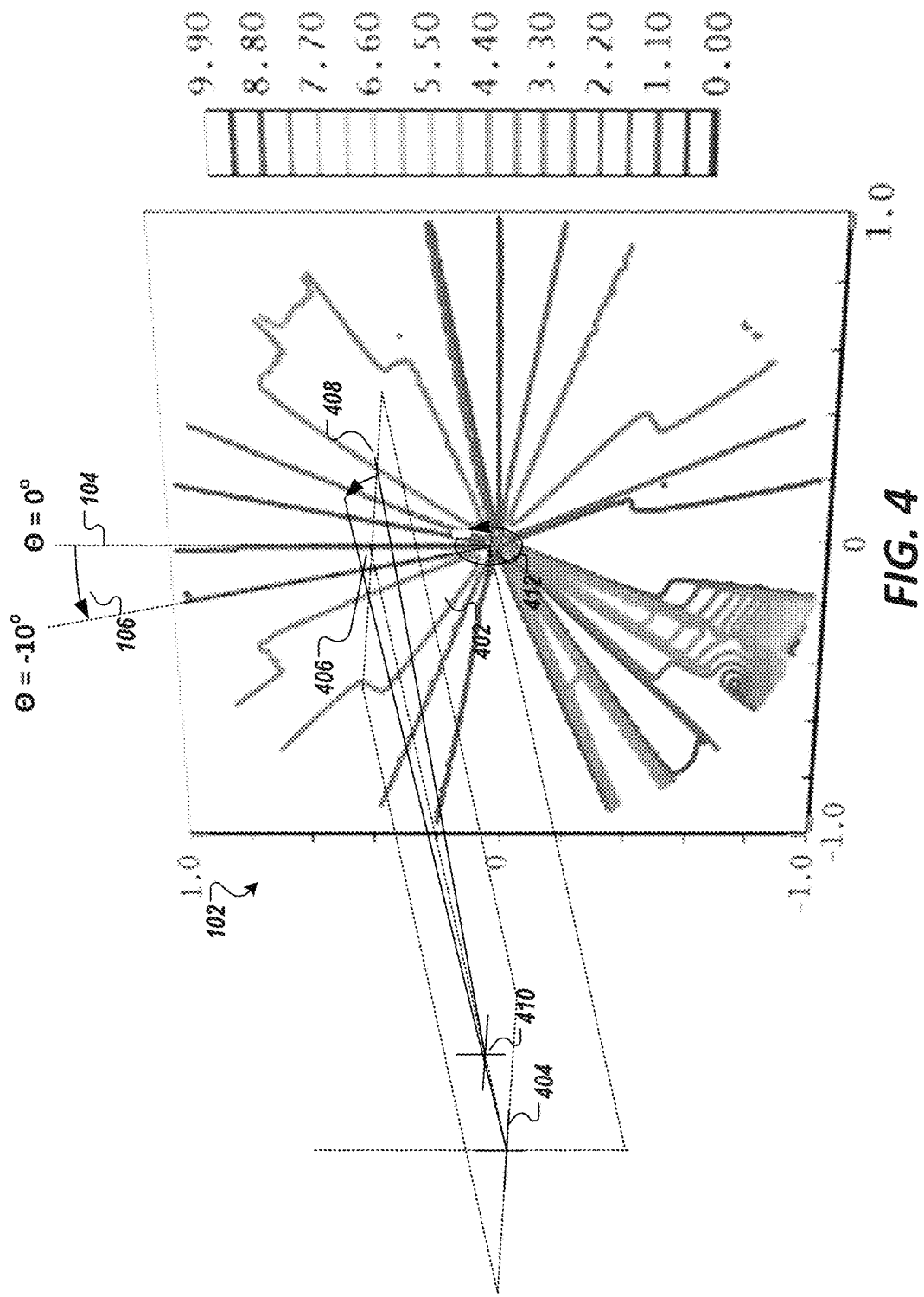
FIG. 4 illustrates an example operation of the polynomial surface of FIG. 1 when subjected to misalignment, in accordance with an illustrative embodiment.

FIG. 4 illustrates an example operation of the polynomial surface 102 of FIG. 1 when subjected to misalignment, in accordance with an illustrative embodiment. The polynomial surface 102, as a diffractive or refractive structure, in some embodiments, varies the extended depth of focus to a plurality of nearby focus points. To this end, light directed to such nearby focus points are thus directed to the desired focus point when the ophthalmic apparatus is subjected to a rotational offset from a primary intended axis of alignment, thereby extending the rotational tolerance of the apparatus to an extended tolerance band. In FIG. 4, a portion (402) of the polynomial surface 102 has a focus point 404 (e.g., referred to as a "main focus point" 404, e.g., to correct for an astigmatism) that is generated by a region about the center 406 of the portion 402 of the polynomial surface 102. In this example, a nearby region 408 of that portion 402 has a focus point 410 (e.g., referred to as an "auxiliary focus point" 410) that is offset from the main focus point 404. When the polynomial surface 102 is rotated about axis 412, e.g., as misalignment 106 is introduced to the corrective meridian Θ=0° (104), the focus point 410 of region 408 is moved towards the main focus point 404, thereby extending the band of operation of the polynomial surface 102. Remarkably, this extended tolerance astigmatism band delivers cylinder power to correct for the astigmatism for a range of meridians (e.g., up to ±10° as shown in FIG. 1, though can be more in other embodiments), thereby eliminating any need for additional corrective measures (e.g., supplemental corrective devices or another surgical intervention) when the implanted ophthalmic apparatus is not perfectly aligned to the desired astigmatism meridian in the eye.

Put another way, the polynomial surface 102 facilitates an extended band of the corrective meridian that has minimal, and/or clinically acceptable, degradation of the visual acuity and modulation transfer function when the ophthalmic apparatus is subjected to rotational misalignment between the astigmatic axis and a center axis of the corrective meridian.

FIG. 5 is a schematic drawing of a top view of a human eye 502, in which the natural lens of the eye 502 has been removed and replaced with an intraocular lens 100 (shown in simplified form in FIG. 6 and in greater detail in FIGS. 6A, 6B, 6C, and 6D). Light enters from the left of FIG. 5, and passes through the cornea 504, the anterior chamber 506, the iris 508, and enters the capsular bag 510. Prior to surgery, the natural lens occupies essentially the entire interior of the capsular bag 510. After surgery, the capsular bag 510 houses the intraocular lens 100, in addition to a fluid that occupies the remaining volume and equalizes the pressure in the eye.

After passing through the intraocular lens, light exits the posterior wall 512 of the capsular bag 510, passes through the posterior chamber 528, and strikes the retina 530, which detects the light and converts it to a signal transmitted through the optic nerve 532 to the brain. The intraocular lens 100 comprises an optic 524 and may include one or more haptics 526 that are attached to the optic 524 and may serve to center the optic 524 in the eye and/or couple the optic 5324 to the capsular bag 510 and/or zonular fibers 520 of the eye.

The optic 524 has an anterior surface 534 and a posterior surface 536, each having a particular shape that contributes to the refractive or diffractive properties of the lens. Either or both of these lens surfaces may optionally have an element made integral with or attached to the surfaces. FIGS. 6A, 6B, 6C, and 6D are schematic diagrams of exemplary ophthalmic apparatuses that include the freeform-polynomial surface area 102, in accordance with an illustrative embodiment. Specifically, FIGS. 6A and 6B show examples of diffractive lenses, and FIGS. 6C and 6D show examples of refractive lenses.

Referring still to FIG. 5, the intraocular lens 100 includes polynomial surface 102 (as a refractive, diffractive, or both) that focus at a plurality of focus points that are offset radially to one another so as to provide an extended tolerance to misalignments of the lens 100 when implanted into the eye 502. That is, when the center axis of a corrective meridian is exactly matched to the desired astigmatic axis, only a first portion of the cylinder axis is focused at the desired point of focus (338) (e.g., at the retina) while second portions of the cylinder axis focuses at other points (540) nearby that are radially offset to the desired point of focus (538). To this end, when the primary axis of the astigmatism of the intraocular lens is rotationally offset (shown as arrow 542) with the astigmatism of the eye, the second portion of the cylinder axis focuses the light to the desired point of focus.

Artificial lenses (e.g., contact lenses or artificial intraocular lenses) can correct for certain visual impairments such as an inability of the natural lens to focus at near, intermediate or far distances; and/or astigmatism. Intraocular toric lenses have the potential for correcting astigmatism while also correcting for other vision impairments such as cataract, presbyopia, etc. However, in some patients, implanted intraocular toric lenses may not adequately correct astigmatism due to rotational misalignment of the corrective meridian of the lenses with the astigmatic meridian. In some patients following the surgical implant of the toric lenses, the corrective meridian of the implanted toric lenses can be rotationally misaligned to the astigmatic meridian, in some instances, by as much as 10 degrees. However, toric lenses that are designed to provide maximum correction (e.g., 1 D to 9 D) at the astigmatic meridian are subject to significant reduction in effectiveness of the correction due to any misalignment from the corrective meridian. In certain designs, it is observed that if the cylindrical power axis were mismatched by 1 degree, there would be about 3 percent reduction of the effectiveness of the correction. The degradation increases with the degree of misalignment. If there were a 10-degree misalignment, there would be about 35% reduction of the effectiveness of the correction. This effect is illustrated in FIG. 7 discussed below.

Figure 7:
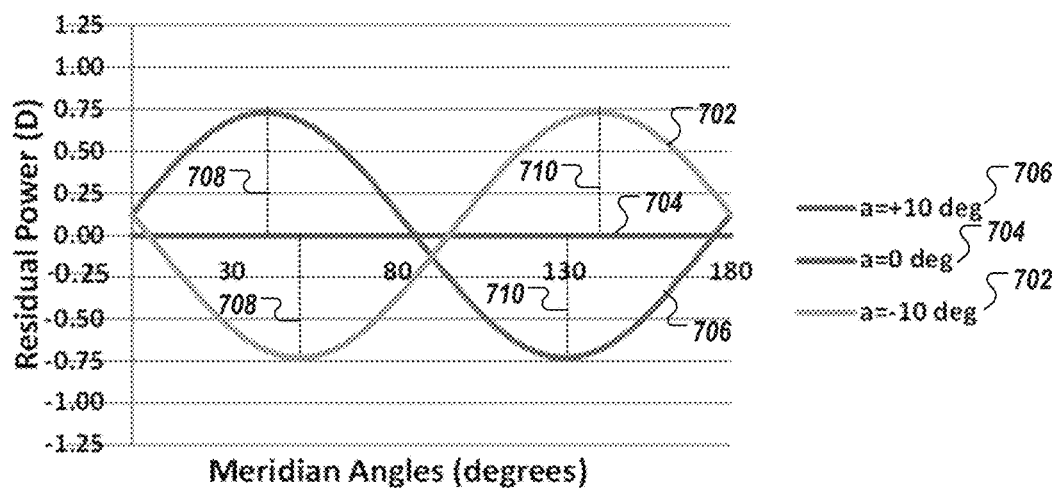
FIGS. 7 and 8 include plots that illustrate the degraded performance of conventional toric lens when subjected to rotational misalignments.
Figure 8:
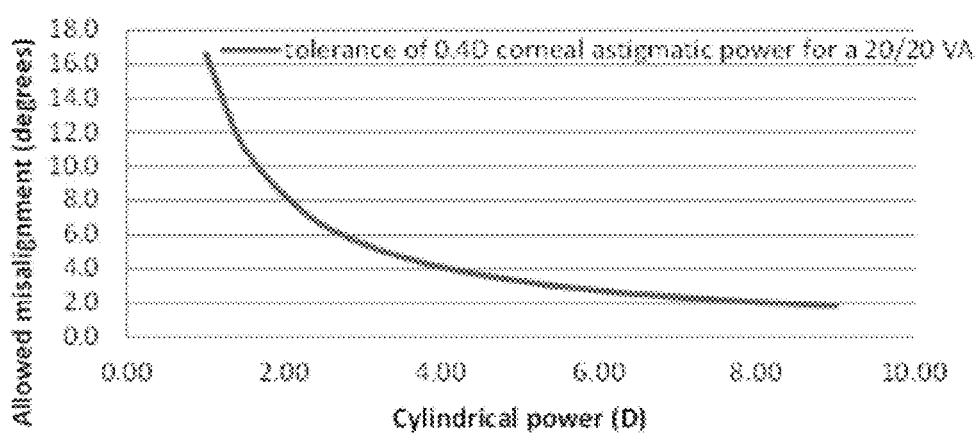

FIGS. 7 and 8 include plots that illustrate the above-discussed degraded performance of conventional toric lens when subjected to rotational misalignments. This conventional toric lens is configured to provide 6.00 Diopters cylinder powers at the IOL plane, 4.11 Diopters cylinder power at the corneal plane, and a corneal astigmatism correction range (i.e., preoperative corneal astigmatism to predicted effects) between 4.00 and 4.75 Diopters.

Referring to FIG. 7, a plot of the undesired meridian power (also referred to as a residual meridian power ("OC")) (shown along the y-axis) added due to the rotational misalignments (shown along the x-axis) of the toric IOL is shown, including the residual powers for i) a negative 10-degree misalignment (shown as line 702), ii) a 0-degree misalignment (shown as line 704), and iii) a positive 10-degree misalignment (shown as line 706). As shown, the undesired added meridian power varies between a maximum of ±0.75 Diopters at around the 45-degree meridian angle (shown as 708) and at about the 135-degree meridian angle (shown as 710). Notably, this undesired added meridian power is outside the tolerance of a healthy human eye, which can tolerant undesired effects up to about 0.4 Diopters (e.g., at the cornea plane) for normal visual acuity (i.e., "20/20 vision"). Because the undesired effects exceeds the astigmatism tolerance of the human eye, corrective prescription glasses, or further surgical operation to correct the implant misalignment, may be necessary to mitigate the effects of the misalignment of such toric IOLs.

This undesired meridian power, conventionally, may be expressed as Equation 1 below.

$$OC = 2\sin\alpha * \frac{c}{2} 0.7 \cos\left(2\left(\theta + 90 + \frac{\alpha}{2}\right)\right) \quad \text{(Equation 1)}$$

As shown in Equation 1, $\theta$ is the correction meridian (also referred to as the cylindrical power axis) (in degrees); C is the astigmatic power (at the IOL plane) to be corrected at meridian $\theta$ (in Diopters); and $\alpha$ is the magnitude of rotational misalignment of the cylindrical power axis to the astigmatic axis (in degrees).

FIG. 8 shows a plot illustrating the tolerance of a toric IOL to misalignment (shown in the y-axis) and a corresponding cylindrical power that may be applied (shown in the x-axis) for each misalignment to not exceed the astigmatism tolerance of the human eye (i.e., degrade the overall visual acuity). The tolerance to misalignment may be calculated as $$|\alpha| \le \sin^{-1}\frac{\frac{0.4}{2}}{\frac{c}{0.7}}$$

where $\alpha$ is the magnitude of rotational misalignment (in degrees). The calculation may be reduced to $$|\alpha| \le \sin^{-1}\frac{0.29}{c}.$$

As shown, for a misalignment of 5 degrees, which is routinely observed in IOL implantations, the correction effectiveness of such IOL implants can only be maintained for a toric IOL with 3.75 Diopters or less. That is, a toric IOL having cylinder power above 3.75 Diopters would exhibit degraded visual acuity due to the residual power exceeding the astigmatism tolerance of a human eye. This effect worsens with further degrees of misalignment. For example, at about 10 degrees, the effectiveness of a toric IOL is greatly reduced where only 1.5 Diopters cylinder power or less can be applied so as to not detrimentally affect the visual acuity. Given that cylinder power of convention toric IOLs may range between 1.00 Diopters and 9.00 Diopters, these toric IOLs are reduced in effectiveness post-operation due to the misalignments of cylinder axis.

Results of IOL with Exemplified Freeform-polynomial Surfaces

Figure 9:
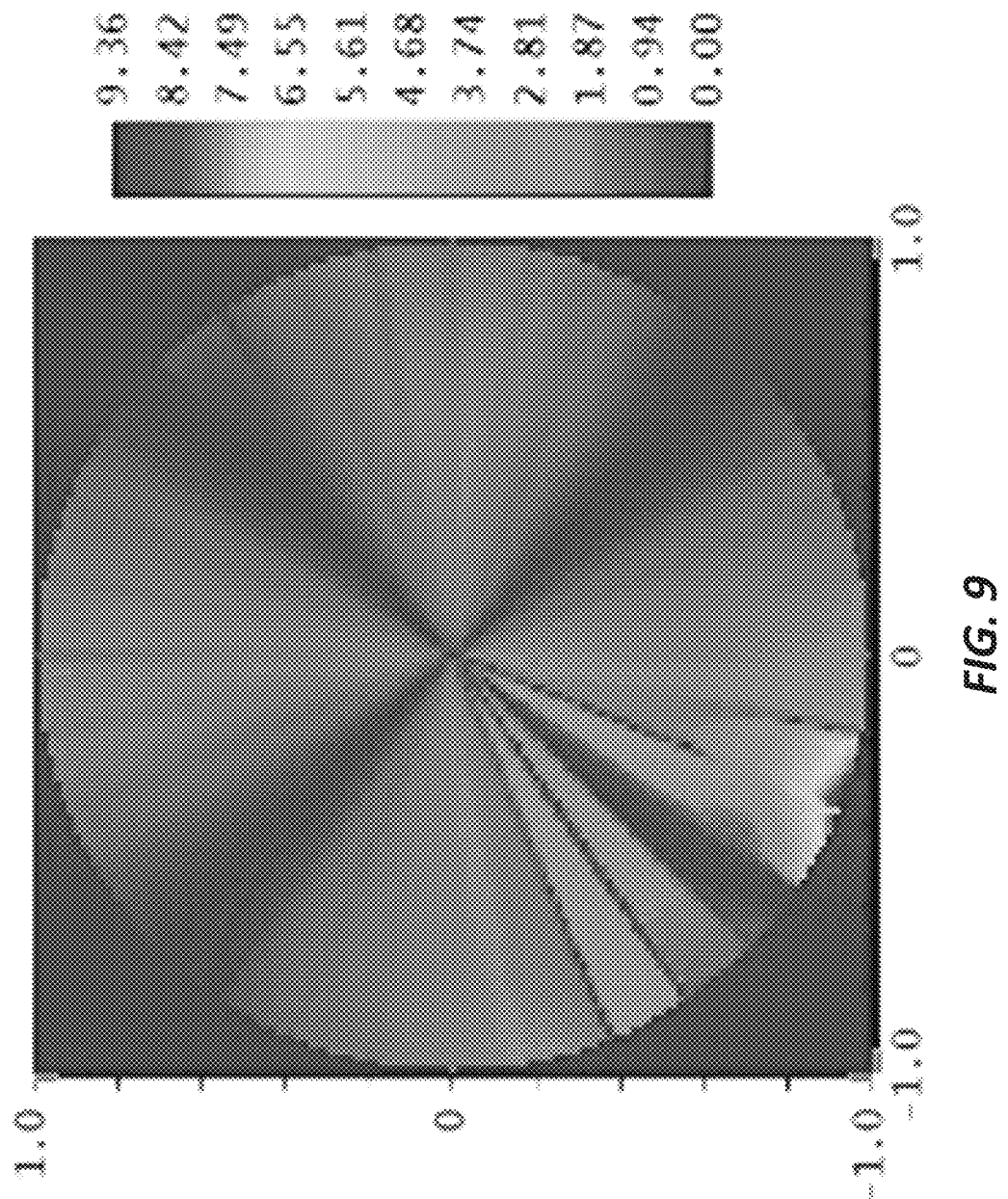
FIG. 9 shows a combined cylinder map generated from the combination of the IOL cylindrical power (provided, in part, via the polynomial surface) combined with the corneal cylindrical power through meridians, in accordance with an illustrative embodiment.
Figure 10:
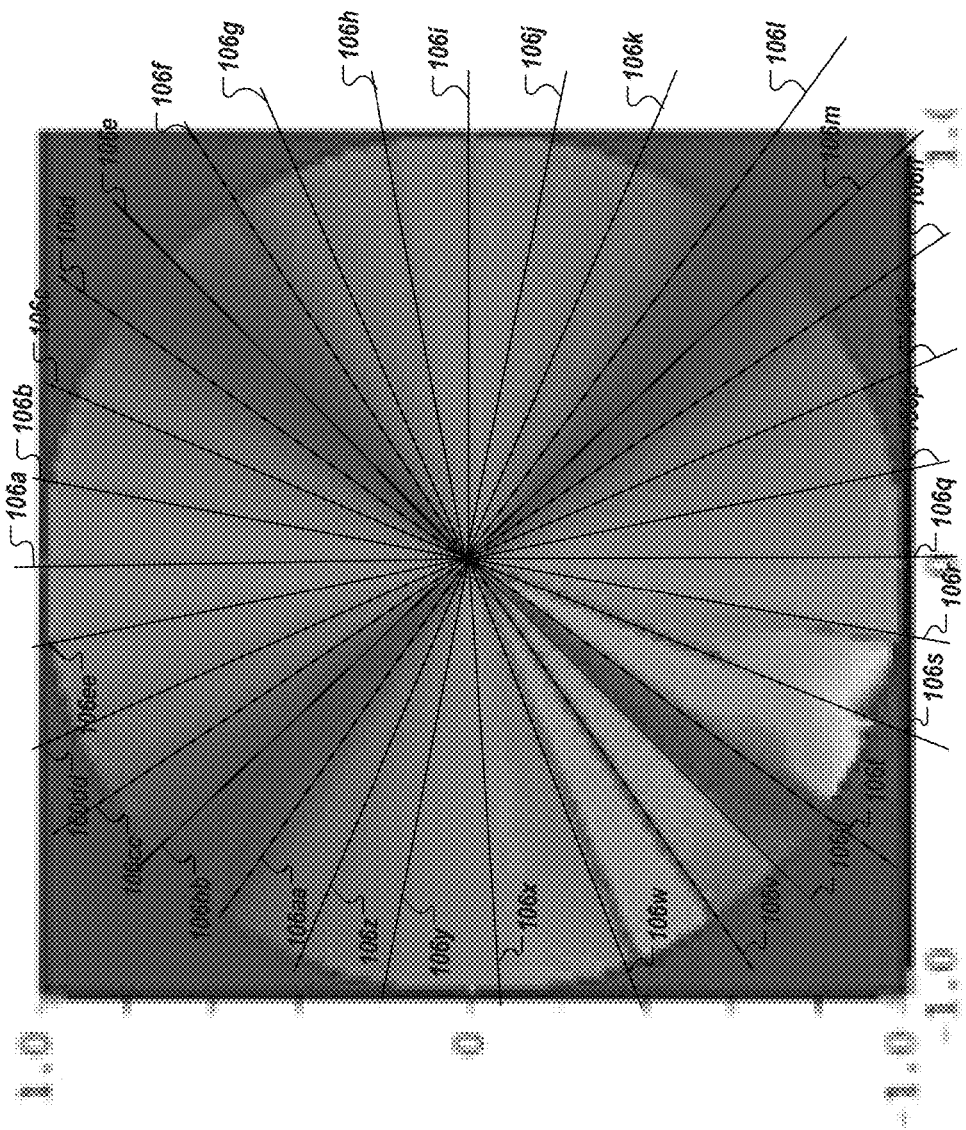
FIG. 10 shows the combined cylinder map of FIG. 9 with the meridians shown in FIG. 2 superimposed thereon, in accordance with an illustrative embodiment.

FIG. 9 shows a combined cylinder map generated from the combination of the IOL cylindrical power (provided, in part, via the polynomial surface) combined with the corneal cylindrical power through meridians. FIG. 10 shows the combined cylinder map of FIG. 9 with the meridians shown in FIG. 2 superimposed thereon.

As discussed above with reference to FIG. 1, and as can be seen from the IOL cylinder map through meridians around the clock, there is remarkably no more than about 0.6 D difference for any continuous uniformly distributed contour lines at the IOL plane. The IOL SE is 20 D at the IOL plane. The IOL cylinder map of FIG. 1 is combined with the IOL SE to provide the overall IOL cylindrical map. That is, the astigmatism associated with test corneal cylindrical power has been attenuated and/or corrected for by the IOL cylindrical power provided, in part, by the polynomial surface.

Figure 11A:
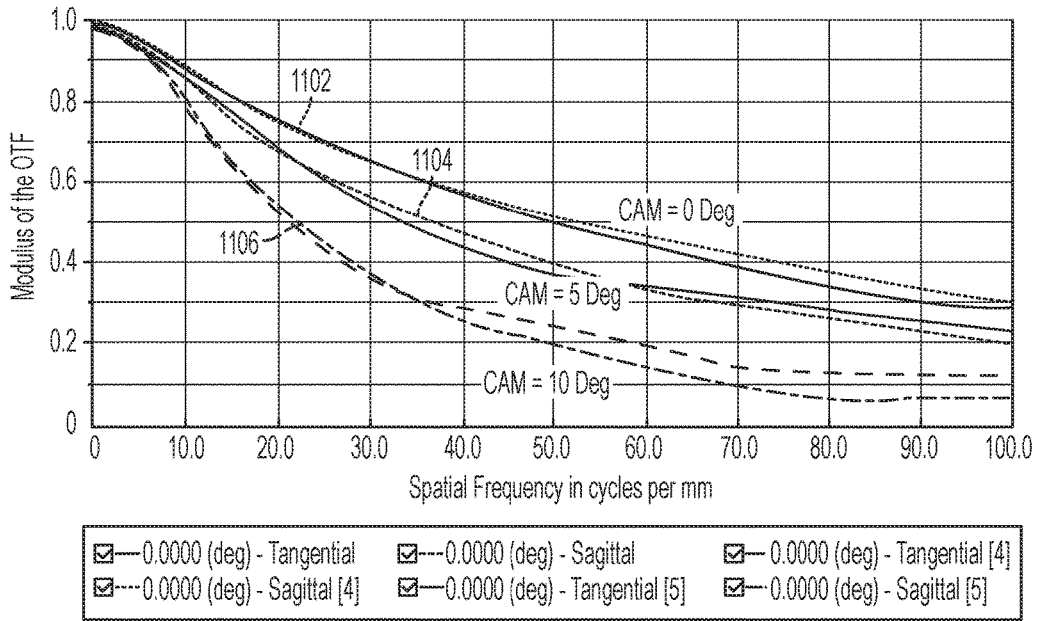
FIGS. 11A and 11B each shows calculated MTF values as spatial frequencies of an exemplified IOL in a physiological eye model with astigmatic cornea in different cylindrical axis misalignment (CAM) situations between the cornea and the IOL for an iris pupil.
Figure 11B:
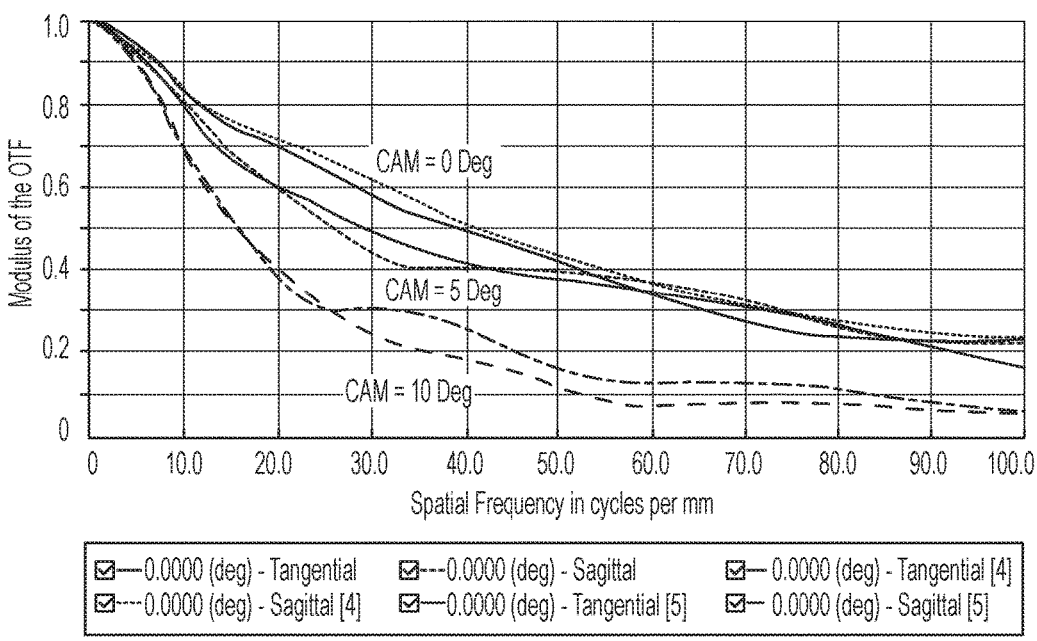

FIGS. 11A and 11B each shows calculated MTF values as spatial frequencies of an exemplified IOL 100 in a physiological eye model with astigmatic cornea in different cylindrical axis misalignment (CAM) situations between the cornea and the IOL for an iris pupil. Notably, as shown in FIGS. 11A and 11B, the modulation transfer function (MTF) is maintained across the extended range of alignment for a lens configured with the freeform-polynomial surface area 102 of FIG. 1. Specifically, in FIGS. 11A and 11B, the MTFs for misalignment at 0 degrees, 5 degrees, and 10 degrees are shown (shown as "CAM=0 Deg" 1102, "CAM=5 Deg" 1104, and "CAM=10 Deg" 1106). In FIG. 11A, the iris pupil is about 3.0 mm. In FIG. 11B, the iris pupil is about 5.0 mm.

Notably, as can also be seen from the MTF curves, there are no cut-offs of the spatial frequency beyond 100 cpd (cycles per degree), which for an IOL with SE (Spherical Equivalent) of 20D (Diopters), this spatial frequency is approximately 30 cpd.

Corneal Irregular Geometry or Limited Retinal Area functions

In another aspect, the polynomial surface 102 of FIG. 1 is optimized to purposely place accumulated high surface amplitude (also referred to high order aberration) to non-functional retinal area so that the functional areas can fully benefit the ETA designs, that is, the enhanced image quality stability. Examples of non-functional retinal areas may include, but not limited to, areas of gradual loss of sight (e.g., associated with glaucoma or retinal macular degeneration (AMD).

Referring to FIG. 2, an accumulated high surface amplitude results at area 208 to provide enhanced image quality stability for the three corrective regions 202, 204, 206 that have uniform distributions discussed herein. In some embodiments, the corrective regions (e.g., 202, 204, 206) effectively span over a region greater than 90 degrees to angular extent. Confined by a finite surface region, it is contemplated that the accumulated (high) surface amplitude area 208 is purposely positioned (in a manner similar to the positioning of the corrective regions 202, 204, 206) to coincide, e.g., with areas of limited retinal functionality that may be present with a given patient. That is, the accumulated (high) surface area is specifically optimized optically to target the special optical needs of the entire eye on this area.

Figure 12:
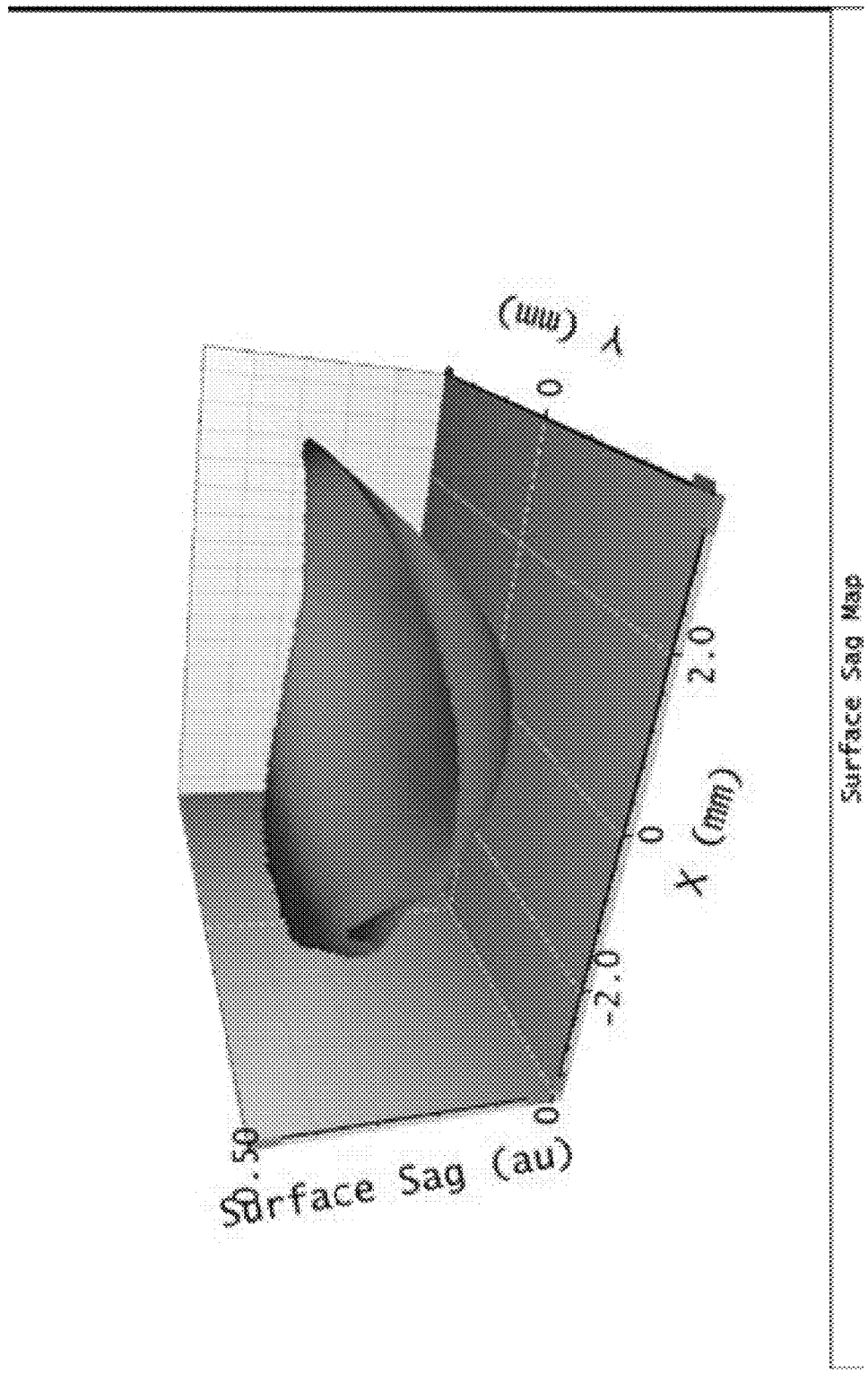
FIG. 12 is a surface SAG map of the polynomial surface of FIG. 1, in accordance with an illustrative embodiment.

FIG. 12 is a surface SAG map of the polynomial surface 102 of FIG. 1, in accordance with an illustrative embodiment.

Figure 13:
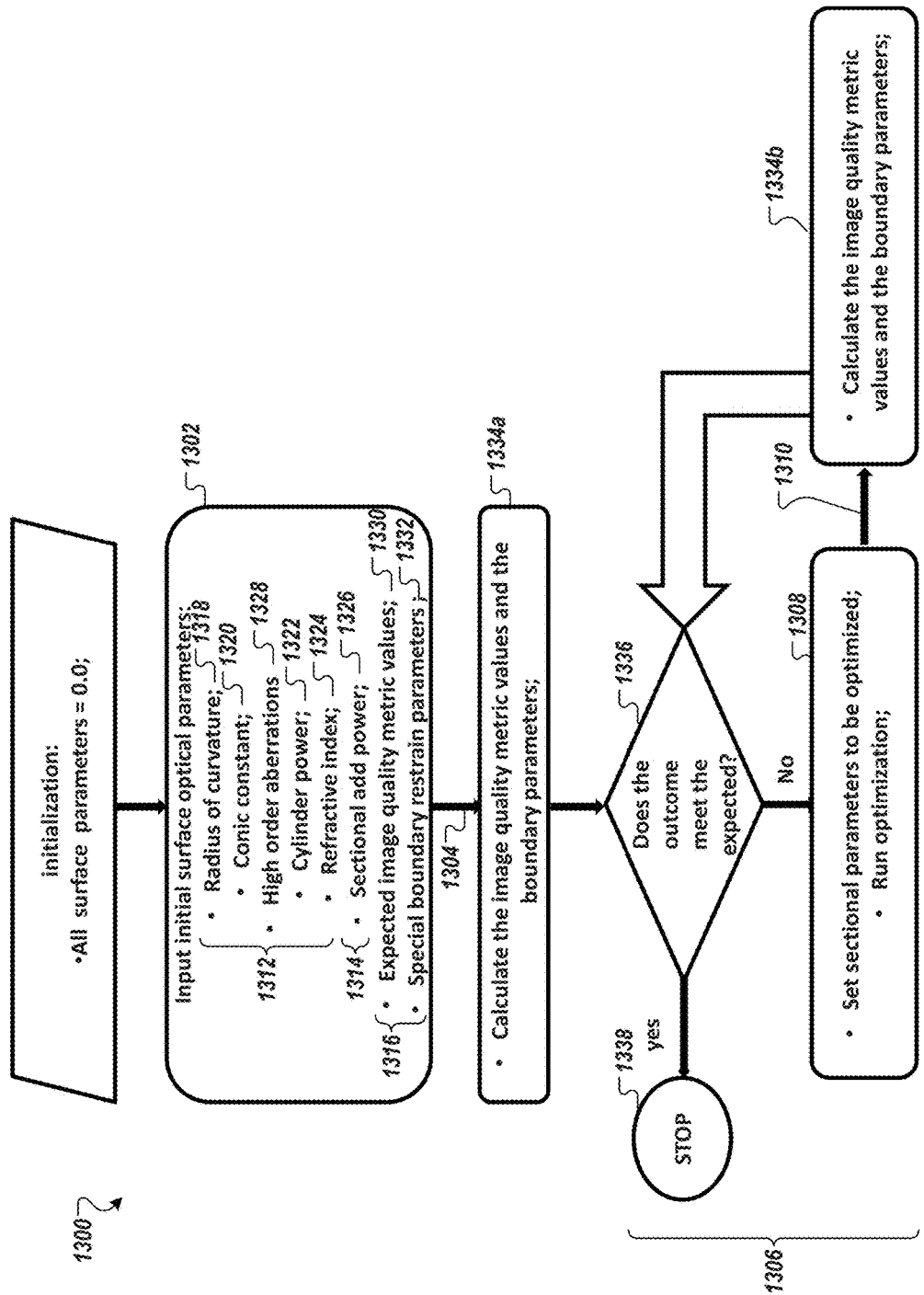
FIG. 13 is diagram of a method to generate the polynomial surface of FIG. 1, in accordance with an illustrative embodiment.

FIG. 13 is diagram of a method 1300 to generate, via a processor, the polynomial surface of FIG. 1, in accordance with an illustrative embodiment. As shown in FIG. 13, the method 1300 includes generating (1302), via a processor, an initial design (1304) comprising a base surface (with base cylindrical power) and sectional enhancements (with added cylindrical power in which each meridian is uniformly arranged for a same given added power) and iteratively generating (1308) and evaluating, a revised design (1310), generated according to an optimization routine (1308) that is performed based on sectional parameters, until pre-defined image quality metric values and boundary parameter are achieved. The sectional enhancements power of the initial design and the iterative design is the ETA polynomial surface of FIG. 1.

Referring still to FIG. 13, the method 1300 includes generating (1302) a first design (1304) via i) initial surface optical parameter, including a) base surface optical parameters 1312 and b) sectional surface optical parameters 1314, and ii) the pre-defined image quality metric values 1316. The base surface optical parameters 1312 include, in some embodiments, parameters associated with a radius of curvature for the toric lens (shown as "Radius of curvature" 1318), parameters associated with conic constant and aspheric coefficients (shown as "Conic constant" 1320), parameters associated with base cylinder power (shown as "Cylinder power" 1322), and parameters associated lens and/or coating material characteristics such as refractive index (shown as "Refractive index" 1324). Other parameters may be used as part of the base surface optical parameters 1312. The section surface optical parameters 1314, in some embodiments, includes parameters associated with sectional added power and meridian characteristics (shown as "Sectional add power" 1328) and parameters associated with high order aberration characteristics, e.g., Zernike aberrations above second-order (shown as "High order aberrations" 1328).

Referring still to FIG. 13, the parameters associated with the sectional added power 1326, in some embodiments, include a cylindrical power, for a given optical zone, for a same given added power in which meridians are uniformly arranged. In some embodiments, the cylindrical power for the added power are all refractive. The parameters associated with the high order aberration characteristics 1328, in some embodiments, include polynomial values (e.g., based on Zernike polynomials, Chebyshev polynomials, and combinations thereof) or characteristics such as polynomial orders and types as well as meridian boundaries for the high order aberrations. The high order aberration is constrained, e.g., from minimum to maximum cylindrical power over one or more meridian sections. In some embodiments, the high order aberrations is constrained or designated to a meridian, e.g., that corresponds to a corneal irregular geometry or limited retinal area functions. In such embodiments, the high order aberrations and its meridian locations on the lens surface may be optimized prior to the meridians for the uniform regions are determined to facilitate a customized design that is tailored for a given patient (i.e., particularly in view of corneal irregular geometry or limited retinal area functions). Such customization has a potential to truly benefit patients having cornea with or without astigmatism, patients with local Keratoconus with or without astigmatism, patients with glaucoma, patients with retinal macular degeneration (AMD), and the like.

Referring still to FIG. 13, the parameters associated with the pre-defined image quality metric value 1316 includes parameters associated with expected image quality metric (shown as "Expected image quality metric values" 1330) and parameters associated with special boundary restrain parameters (shown as "Special boundary restrain parameters" 1332). In some embodiments, image quality metric is based a comparison of a base polychromatic diffraction MTF (modular transfer function) (e.g., tangential and sagittal) to a number of error polychromatic diffraction MTFs values, e.g., where one or more polychromatic diffraction MTFs are determined for one or more misalignments of the generated toric lens from its intended operating meridians, e.g., at 5-degree misalignment and at 10-degree misalignment.

Referring still to FIG. 13, the initial design (1304) is evaluated (1334*a*) to determine image quality metric values (e.g., the base polychromatic diffraction MTF, e.g., at 0 degree misalignment) and the error polychromatic diffraction MTFs, e.g., at the 5 and 10 degrees misalignment) and boundary parameters, e.g., as shown in FIGS. 11A and 11B. The determined image quality metric values are evaluated (1336) to determine whether the image quality metric values and boundary parameters meet an expected outcome, e.g., a value of 0.2. In some embodiments, the expected outcome is whether there is no cut off through spatial frequency beyond 100 cpd. Upon determining that the condition is met, the method 1300 is stop (1338). It is contemplated that other image quality metrics may be used, e.g., the optical transfer function (OTF), phase transfer function (PhTF), and etc.

Where the condition is not met, the method 1300 adjusts (1308) sectional parameters to be optimized and rerun the optimization to generate the revised design 1310. The adjusted sectional parameters may include meridians locations and meridian spacing among neighboring meridians. The optimization may include allowing the uniform contour lines to move from one meridian to a next meridian up based on an upper limit amount and a lower limit amount. As shown in FIG. 2, the uniform contour line 210 is show transitioning from meridian 106*m* to meridian 106*n*. The transition is constrained to occur along a specific radial position and without abrupt transition points.

Referring back to FIG. 13, the method 1300 then includes evaluating (1334*b*) the revised design 1310 to determine image quality metric values (e.g., the base polychromatic diffraction MTF, e.g., at 0 degree misalignment) and the error polychromatic diffraction MTFs, e.g., at the 5 and 10 degrees misalignment) and boundary parameters, as discussed in relation to step 1334*a*, and re-evaluating (1336) whether the revised image quality metric values and boundary parameters meet the expected outcome, as discussed in relation to step 1336.

In some embodiments, the method 1300 is performed in an optical and illumination design tool such as Zemax (Kirkland, Wash.). It is contemplated that the method 1300 can be performed in other simulation and/or design environment.

The present technology may be used, for example, in the Tecnis toric intraocular lens product line as manufactured by Abbott Medical Optics, Inc. (Santa Ana, Calif.).

It is not the intention to limit the disclosure to embodiments disclosed herein. Other embodiments may be used that are within the scope and spirit of the disclosure. In some embodiments, the above disclosed angularly varying phase members may be used for multifocal toric, extended range toric, and other categorized IOLs for extended tolerance of astigmatism caused by factors including the cylindrical axis misalignment. In addition, the above disclosed angularly varying phase members may be applied to spectacle, contact lens, corneal inlay, anterior chamber IOL, or any other visual device or system.

Exemplary Computer System

Figure 14:
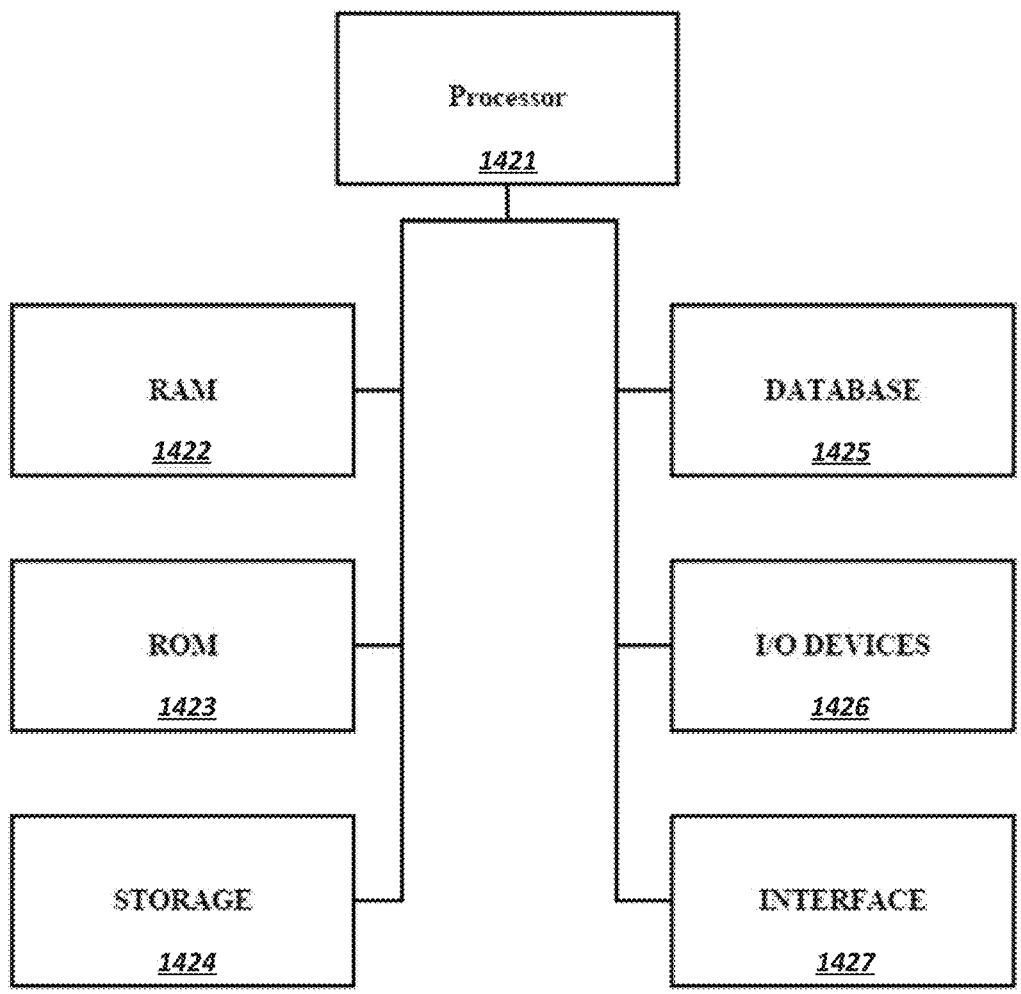
FIG. 14 is a diagram of an example computing device configured to generate the polynomial surface disclosed herein.

FIG. 14 is a diagram of an example computing device configured to generate the polynomial surface disclosed herein. As used herein, "computer" may include a plurality of computers. The computers may include one or more hardware components such as, for example, a processor 1421, a random access memory (RAM) module 1422, a read-only memory (ROM) module 1423, a storage 1424, a database 1425, one or more input/output (I/O) devices 1426, and an interface 1427. Alternatively and/or additionally, controller 1420 may include one or more software components such as, for example, a computer-readable medium including computer executable instructions for performing a method associated with the exemplary embodiments. It is contemplated that one or more of the hardware components listed above may be implemented using software. For example, storage 1424 may include a software partition associated with one or more other hardware components. It is understood that the components listed above are exemplary only and not intended to be limiting.

Processor 1421 may include one or more processors, each configured to execute instructions and process data to perform one or more functions associated with a computer for indexing images. Processor 1421 may be communicatively coupled to RAM 1422, ROM 1423, storage 1424, database 1425, I/O devices 1426, and interface 1427. Processor 1421 may be configured to execute sequences of computer program instructions to perform various processes. The computer program instructions may be loaded into RAM 1422 for execution by processor 1421. As used herein, processor refers to a physical hardware device that executes encoded instructions for performing functions on inputs and creating outputs.

RAM 1422 and ROM 1423 may each include one or more devices for storing information associated with operation of processor 1421. For example, ROM 1423 may include a memory device configured to access and store information associated with controller 1420, including information associated with IOL lenses and their parameters. RAM 1422 may include a memory device for storing data associated with one or more operations of processor 1421. For example, ROM 1423 may load instructions into RAM 1422 for execution by processor 1421.

Storage 1424 may include any type of mass storage device configured to store information that processor 1421 may need to perform processes consistent with the disclosed embodiments. For example, storage 1424 may include one or more magnetic and/or optical disk devices, such as hard drives, CD-ROMs, DVD-ROMs, or any other type of mass media device.

Database 1425 may include one or more software and/or hardware components that cooperate to store, organize, sort, filter, and/or arrange data used by controller 1420 and/or processor 1421. For example, database 1425 may store hardware and/or software configuration data associated with input-output hardware devices and controllers, as described herein. It is contemplated that database 1425 may store additional and/or different information than that listed above.

I/O devices 1426 may include one or more components configured to communicate information with a user associated with controller 1420. For example, I/O devices may include a console with an integrated keyboard and mouse to allow a user to maintain a database of images, update associations, and access digital content. I/O devices 1426 may also include a display including a graphical user interface (GUI) for outputting information on a monitor. I/O devices 1426 may also include peripheral devices such as, for example, a printer for printing information associated with controller 1420, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1427 may include one or more components configured to transmit and receive data via a communication network, such as the Internet, a local area network, a workstation peer-to-peer network, a direct link network, a wireless network, or any other suitable communication platform. For example, interface 1427 may include one or more modulators, demodulators, multiplexers, demultiplexers, network communication devices, wireless devices, antennas, modems, and any other type of device configured to enable data communication via a communication network.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

What is claimed is:

1. A rotationally-tolerant intraocular lens (IOL), the intraocular lens having regions of one or more base spherical powers and one or more cylinder powers that are added to the one or more base spherical power for correcting an astigmatism, the intraocular lens comprising a multi-zonal lens body comprising one or more angularly-varying phase members that each includes an optimized combination of angularly and zonally refractive, or an optimized combination of angularly and zonally diffractive, phase structure located across one or more optical zones to apply cylinder power at one or more correcting meridian, wherein each of the one or more angularly-varying phase members applies the cylinder power at a given correcting meridian and varies an extended depth of focus to a plurality of nearby points of focus to provide an extended tolerance to misalignment of the intraocular lens when implanted in an eye, wherein the multi-zonal lens body forms a first angularly-varying phase member having a peak cylinder power centered at a first meridian, the first angularly-varying phase member being defined as a polynomial-based surface having a plurality of meridian of distinct cylinder powers, wherein the polynomial-based surface has a peak cylinder power that is coincident at a meridian, including a first correcting meridian, wherein light incident to a given region of the first correcting meridian, and respective regions nearby, is directed to a given point of focus such that the regions nearby to the given region direct light to the given point of focus when the given meridian is rotationally offset from the given region, thereby establishing an extended band of operational meridians over the first correcting meridian, and wherein each phase structure has a height profile at a face of the multi-zonal lens body that varies along the extended band of operational meridians over each respective correcting meridian, and wherein each of the plurality of meridians is uniformly arranged on the one or more optical zones fora same given added diopter of power up to 1.0 D (diopters).

2. The rotationally-tolerant intraocular lens of claim 1, wherein differences in added cylinder power between each given meridian of the plurality of meridians and each neighboring meridian is less than about 0.6 D (diopters).

3. The rotationally-tolerant intraocular lens of claim 1, wherein the same given added diopter is about 0.5 D (diopters).

4. The rotationally-tolerant intraocular lens of claim 1, wherein the polynomial-based surface establishes the extended band of operation across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

5. The rotationally-tolerant intraocular lens of claim 1, wherein the polynomial-based surface is characterized by a series of weighted cosine-based functions.

6. The rotationally-tolerant intraocular lens of claim 1, wherein the plurality of meridians include a first meridian, a second meridian, and a third meridian, each having the extended band of operation of at least 10 degrees.

7. The rotationally-tolerant intraocular lens of claim 6, wherein a first center of the first meridian is angularly spaced about 90 degrees to a second center of the second meridian.

8. The rotationally-tolerant intraocular lens of claim 6, wherein the optical zone comprises a fourth meridian having an accumulated high surface amplitude such that the first meridian, the second meridian, and the third meridian have the established extended band of operation.

9. The rotationally-tolerant intraocular lens of claim 8, wherein the fourth meridian is purposely positioned at an angular position that coincides with a diagnosed limited retinal functional area of a patient.

10. The rotationally-tolerant intraocular lens of claim 1, wherein the polynomial-based surface comprises a refractive surface.

11. The rotationally-tolerant intraocular lens of claim 1, wherein the polynomial-based surface comprises a diffractive surface.

12. The rotationally-tolerant intraocular lens of claim 1, wherein an offset of each meridian of the plurality of meridians of about 10 degrees causes a MTF (modulation transfer function) measure change of less than 10% at 30 cycles per degree (cpd).

13. The rotationally-tolerant intraocular lens of claim 1, wherein the polynomial-based surface at a first meridian and at a second meridian comprises a bifocal lens.

14. The rotationally-tolerant intraocular lens of claim 1, wherein the polynomial-based surface at a first meridian comprises a monofocal lens.

15. The rotationally-tolerant intraocular lens of claim 1, wherein the polynomial-based surface at a first meridian comprises an extended range lens.

16. The rotationally-tolerant intraocular lens of claim 1, comprising: an accumulated high surface amplitude area disposed at coordinates that coincides with non-functional or limited functional retinal regions of a given patient.

* * * * *